United States Patent
Ramos De Miguel et al.

(10) Patent No.: US 11,806,530 B2
(45) Date of Patent: Nov. 7, 2023

(54) BALANCE COMPENSATION

(71) Applicants: Cochlear Limited, Macquarie University (AU); University of Las Palmas de Gran Canaria, Las Palmas de Gran Canaria (ES)

(72) Inventors: Angel Ramos De Miguel, Las Palmas (ES); Carl Van Himbeeck, Zottegem (BE); Erika Jeanne Van Baelen, Heverlee (BE)

(73) Assignees: Cochlear Limited, Macquarie University (AU); University of Las Palmas de Gran Canaria, Las Palmas de Gran Canaria (ES)

( * ) Notice: Subject to any disclaimer, the term of this patent is extended or adjusted under 35 U.S.C. 154(b) by 0 days.

(21) Appl. No.: 16/953,765

(22) Filed: Nov. 20, 2020

(65) Prior Publication Data

US 2021/0322772 A1    Oct. 21, 2021

(30) Foreign Application Priority Data

Apr. 21, 2020    (EP) .................................... 20382323

(51) Int. Cl.
*A61N 1/36* (2006.01)
*A61N 1/05* (2006.01)

(52) U.S. Cl.
CPC ....... *A61N 1/36038* (2017.08); *A61N 1/0541* (2013.01)

(58) Field of Classification Search
CPC .......... A61N 1/05; A61N 1/0541; A61N 1/36; A61N 1/36038
See application file for complete search history.

(56) References Cited

U.S. PATENT DOCUMENTS

| | | | | |
|---|---|---|---|---|
| 1,146,292 A | * | 7/1915 | Wappler ............. | A61B 17/3478 607/116 |
| 4,819,647 A | * | 4/1989 | Byers ................... | G09B 21/009 607/116 |

(Continued)

FOREIGN PATENT DOCUMENTS

| WO | WO2000066215 A1 | 11/2000 |
|---|---|---|
| WO | WO2001060282 A2 | 8/2001 |

(Continued)

OTHER PUBLICATIONS

Extended European Search Report in counterpart European Application No. EP20208874.6, dated Apr. 23, 2021, 9 pages.

(Continued)

*Primary Examiner* — Christopher A Flory
(74) *Attorney, Agent, or Firm* — Edell, Shapiro & Finnan, LLC

(57) ABSTRACT

Disclosed technology includes technology for compensating for a balance dysfunction. A system can combine sensory substitution with balance dysfunction suppression. Dysfunctional balance information coming from a recipient's vestibular system is inhibited using stimulation. Balance information (e.g. how the recipient is positioned with respect to gravity, such as rotation along pitch and roll axes) is then passed to another sensory channel (e.g., visual, audible, or tactile sensory channels). Such a system can be implemented with a cochlear implant or another sensory prostheses having balance signals injected into the stimulation signal processing path.

23 Claims, 7 Drawing Sheets

(56) References Cited

U.S. PATENT DOCUMENTS

| | | | |
|---|---|---|---|
| 4,850,962 A | 7/1989 | Schaefer | |
| 5,123,422 A * | 6/1992 | Charvin | A61N 1/0541 607/137 |
| 5,545,219 A * | 8/1996 | Kuzma | A61F 11/20 607/137 |
| 5,919,149 A | 7/1999 | Allum | |
| 6,078,841 A * | 6/2000 | Kuzma | A61N 1/0541 607/137 |
| 6,119,044 A * | 9/2000 | Kuzma | A61N 1/0541 607/137 |
| 6,125,302 A * | 9/2000 | Kuzma | A61N 1/0541 607/137 |
| 6,149,657 A * | 11/2000 | Kuzma | A61N 1/0541 607/137 |
| 6,163,729 A * | 12/2000 | Kuzma | A61N 1/0541 607/137 |
| 6,195,586 B1 * | 2/2001 | Kuzma | A61N 1/0541 607/137 |
| 6,304,787 B1 | 10/2001 | Kuzma et al. | |
| 6,374,143 B1 * | 4/2002 | Berrang | A61N 1/0541 607/137 |
| 6,383,150 B1 | 5/2002 | Stewart et al. | |
| 6,421,569 B1 | 7/2002 | Treaba et al. | |
| 6,546,291 B2 | 4/2003 | Merfeld et al. | |
| 7,146,227 B2 | 12/2006 | Dadd et al. | |
| 7,225,028 B2 | 5/2007 | Della Santina et al. | |
| 7,231,257 B2 | 6/2007 | McDermott et al. | |
| 7,269,461 B2 | 9/2007 | Dadd et al. | |
| 7,272,449 B2 | 9/2007 | Dadd et al. | |
| 7,382,850 B2 | 6/2008 | Zierhofer | |
| 7,451,000 B2 | 11/2008 | Gibson et al. | |
| 7,555,352 B2 | 6/2009 | Dadd et al. | |
| 7,561,709 B2 | 7/2009 | Vandali et al. | |
| 7,647,120 B2 | 1/2010 | Della Santina et al. | |
| 7,782,358 B2 | 8/2010 | Nieminen et al. | |
| 7,792,586 B2 | 9/2010 | Dadd et al. | |
| 7,801,617 B2 | 9/2010 | Dijk et al. | |
| 7,822,487 B2 | 10/2010 | Dadd et al. | |
| 7,860,573 B2 | 12/2010 | van den Honert | |
| 7,867,140 B2 | 1/2011 | Chiari et al. | |
| 7,894,916 B2 | 2/2011 | Gibson et al. | |
| 7,933,654 B2 | 4/2011 | Merfeld et al. | |
| 7,974,711 B2 | 7/2011 | Dadd et al. | |
| 7,974,712 B2 | 7/2011 | Gibson et al. | |
| 7,983,767 B2 | 7/2011 | Dadd et al. | |
| 7,983,768 B2 | 7/2011 | Dadd et al. | |
| 8,103,362 B2 | 1/2012 | Dadd et al. | |
| 8,249,724 B2 | 8/2012 | Risi et al. | |
| 8,265,773 B2 | 9/2012 | Dadd et al. | |
| 8,301,269 B2 | 10/2012 | Gibson et al. | |
| 8,355,793 B2 | 1/2013 | Dadd et al. | |
| 8,396,570 B2 | 3/2013 | Dadd et al. | |
| 8,454,529 B2 | 6/2013 | Daly et al. | |
| 8,460,315 B2 | 6/2013 | Gibson et al. | |
| 8,617,097 B2 | 12/2013 | Dadd et al. | |
| 8,620,459 B2 | 12/2013 | Gibson et al. | |
| 8,751,019 B2 | 6/2014 | Dadd et al. | |
| 8,764,676 B2 | 7/2014 | Prakash et al. | |
| 8,768,484 B2 | 7/2014 | Della Santina et al. | |
| 8,782,884 B2 | 7/2014 | Capcelea et al. | |
| 8,805,546 B2 | 8/2014 | Dadd et al. | |
| 8,855,774 B2 | 10/2014 | Soto-Eguibar et al. | |
| 8,868,202 B2 | 10/2014 | Della Santina et al. | |
| 8,909,349 B2 | 12/2014 | Dadd et al. | |
| 8,965,520 B2 | 2/2015 | Botros et al. | |
| 9,031,661 B2 | 5/2015 | Smith et al. | |
| 9,084,893 B2 | 7/2015 | Vandali et al. | |
| 9,089,692 B2 | 7/2015 | Risi et al. | |
| 9,101,732 B2 | 8/2015 | Dadd et al. | |
| 9,144,677 B2 | 9/2015 | Garnham et al. | |
| 9,173,585 B2 | 11/2015 | Tsampazis et al. | |
| 9,211,407 B2 | 12/2015 | Della Santina et al. | |
| 9,242,094 B2 | 1/2016 | Della Santina et al. | |
| 9,338,567 B2 | 5/2016 | Mauger et al. | |
| 9,339,649 B2 | 5/2016 | Cushing et al. | |
| 9,352,144 B2 | 5/2016 | Paul et al. | |
| 9,415,208 B2 | 8/2016 | Dadd et al. | |
| 9,427,568 B2 | 8/2016 | Dadd et al. | |
| 9,473,852 B2 | 10/2016 | Buyens | |
| 9,511,226 B2 | 12/2016 | Pelizzone et al. | |
| 10,052,062 B2 | 8/2018 | De Sapio et al. | |
| 10,207,101 B2 | 2/2019 | Galea et al. | |
| 10,220,201 B2 | 3/2019 | Mauch et al. | |
| 10,225,671 B2 | 3/2019 | Goorevich et al. | |
| 10,231,648 B2 | 3/2019 | Plotnik-Peleg et al. | |
| 10,307,084 B2 | 6/2019 | Forth et al. | |
| 10,342,461 B2 | 7/2019 | Basta et al. | |
| 10,368,770 B2 | 8/2019 | Lithgow | |
| 10,398,897 B2 | 9/2019 | Owen et al. | |
| 10,413,728 B2 | 9/2019 | Carter et al. | |
| 10,543,125 B2 | 1/2020 | Dadd et al. | |
| 2002/0029074 A1 * | 3/2002 | Treaba | A61N 1/0541 607/137 |
| 2003/0045921 A1 * | 3/2003 | Dadd | A61N 1/0541 607/137 |
| 2003/0125785 A1 * | 7/2003 | Kuzma | A61N 1/0541 607/116 |
| 2003/0181967 A1 * | 9/2003 | Dadd | A61N 1/0541 607/122 |
| 2004/0122501 A1 * | 6/2004 | Dadd | A61N 1/0541 607/137 |
| 2004/0127968 A1 * | 7/2004 | Kuzma | A61N 1/0541 607/137 |
| 2004/0220651 A1 * | 11/2004 | Kuzma | A61N 1/0541 607/125 |
| 2004/0230254 A1 | 11/2004 | Harrison et al. | |
| 2004/0234089 A1 | 11/2004 | Rembrand et al. | |
| 2004/0243212 A1 * | 12/2004 | Dadd | A61N 1/0541 607/137 |
| 2005/0131272 A1 | 6/2005 | Waldmann | |
| 2005/0240253 A1 | 10/2005 | Tyler et al. | |
| 2005/0267549 A1 * | 12/2005 | Della Santina | A61N 1/372 607/57 |
| 2006/0235500 A1 | 10/2006 | Gibson et al. | |
| 2007/0208403 A1 | 9/2007 | Della Santina et al. | |
| 2009/0240099 A1 | 9/2009 | Conn | |
| 2009/0306457 A1 | 12/2009 | Parker et al. | |
| 2010/0198301 A1 | 8/2010 | Smith | |
| 2010/0324355 A1 | 12/2010 | Spitaels et al. | |
| 2011/0046435 A1 | 2/2011 | Jensen et al. | |
| 2011/0082521 A1 | 4/2011 | Botros et al. | |
| 2012/0078337 A1 | 3/2012 | Darley et al. | |
| 2012/0130465 A1 | 5/2012 | Risi et al. | |
| 2012/0150294 A1 | 6/2012 | Weinberg et al. | |
| 2012/0158112 A1 | 6/2012 | Jolly et al. | |
| 2012/0226187 A1 | 9/2012 | Bierer et al. | |
| 2012/0277835 A1 | 11/2012 | Della Santina et al. | |
| 2013/0066424 A1 | 3/2013 | Hessler et al. | |
| 2013/0096654 A1 | 4/2013 | Jager et al. | |
| 2013/0120147 A1 | 5/2013 | Narasimhan et al. | |
| 2013/0184788 A1 | 7/2013 | Jager et al. | |
| 2014/0026664 A1 | 1/2014 | Gannot et al. | |
| 2015/0032186 A1 | 1/2015 | Cushing et al. | |
| 2015/0039057 A1 | 2/2015 | Della Santina et al. | |
| 2015/0066126 A1 | 3/2015 | Marx et al. | |
| 2015/0256948 A1 | 9/2015 | Nielsen | |
| 2016/0066821 A1 | 3/2016 | Mestrovic et al. | |
| 2016/0203692 A1 | 7/2016 | Ten Kate et al. | |
| 2016/0220153 A1 | 8/2016 | Annegarn et al. | |
| 2016/0310738 A1 | 10/2016 | Mauch et al. | |
| 2017/0035343 A1 | 2/2017 | Curtiss | |
| 2017/0080212 A1 | 3/2017 | Dadd et al. | |
| 2017/0172465 A1 | 6/2017 | Osorio | |
| 2017/0303849 A1 | 10/2017 | De Sapio et al. | |
| 2017/0359659 A1 | 12/2017 | Von Brasch et al. | |
| 2018/0021568 A1 | 1/2018 | Schachtele et al. | |
| 2018/0178025 A1 * | 6/2018 | Mukesh | A61N 2/006 |
| 2018/0280687 A1 | 10/2018 | Carter et al. | |
| 2018/0304077 A1 | 10/2018 | Lee et al. | |
| 2019/0167977 A1 | 6/2019 | Risi et al. | |
| 2020/0046978 A1 | 2/2020 | Kaufmann et al. | |

(56) References Cited

U.S. PATENT DOCUMENTS

FOREIGN PATENT DOCUMENTS

| WO | WO2002047547 A1 | 6/2002 |
|---|---|---|
| WO | WO2003070322 A1 | 8/2003 |
| WO | WO2013134873 A1 | 9/2013 |
| WO | WO2014165462 A1 | 10/2014 |
| WO | WO2015077773 A1 | 5/2015 |
| WO | WO2017081335 A1 | 5/2017 |
| WO | WO2019073348 A2 | 4/2019 |
| WO | WO2019173107 A1 | 9/2019 |

OTHER PUBLICATIONS

"Medication." Retrieved from the Internet: <URL: https://vestibular.org/article/diagnosis-treatment/treatments/medication/>, 6 pages, Retrieved on Jan. 22, 2020.
"Author Index," Audiology & Neurotology, vol. 25, No. 1-2, p. 109, dated 2020.
Afzal et al., "Evaluating the effects of kinesthetic biofeedback delivered using reaction wheels on standing balance." Journal of healthcare engineering. Jun. 11, 2018; vol. 2018, 10 pages.
Alhasan et al., "The effect of visual biofeedback on balance in elderly population: a systematic review." Clinical interventions in aging. 2017;12:487-497.
An interim exploitation plan. Grant Agreement No. 801127, "European Development of Bionic Vestibular Implant For Bilateral Vestibular Dysfunction," Nov. 15, 2019, 20 pages.
Broadcasting and communication plan of project results, Grant Agreement No. 801127, "European Development of Bionic Vestibular Implant For Bilateral Vestibular Dysfunction," Nov. 31, 2018, 46 pages.
Cochlear, "Nucleus Freedom implant with Straight electrode," Surgeon's Guide, 28 pages, dated 2016.
Data management plan RPT1, Grant Agreement No. 801127, "European Development of Bionic Vestibular Implant For Bilateral Vestibular Dysfunction," Feb. 31, 2019, 10 pages.
Emami et al., "Saccular Dysfunction in Low-Frequency Age-Related Sensorineural Hearing Loss," 5 pages, Apr. 10, 2017.
Emami et al., "Vestibular hearing and neural synchronization." ISRN otolaryngology. vol. 2012, 6 pages, dated 2012.
Emami, "Hypersensitivity of vestibular system to sound and pseudoconductive hearing loss in deaf patients," International Scholarly Research Notices. vol. 2014, 5 pages, dated 2014.
Hageman et al., "Design of a vestibular prosthesis for sensation of gravitoinertial acceleration." Journal of Medical Devices. Sep. 1, 2016;10(3), 3 pages.
Harris, "New Concepts in Electrical Stimulation in Vestibular Dysfunction." Audiology and Neurotology. 2020;25(1-2) p. 5.
Hsieh et al., "A wearable walking monitoring system for gait analysis." In 2012 Annual International Conference of the EEE Engineering in Medicine and Biology Society Aug. 28, 2012 (pp. 6772-6775). IEEE.
Mirelman et al., "Audio-biofeedback training for posture and balance in patients with Parkinson's disease. Journal of neuroengineering and rehabilitation." Dec. 1, 2011;8(1):35, 7 pages.
Ramos de Miguel et al., "Vestibular response to electrical stimulation of the otolith organs. implications in the development of a vestibular implant for the improvement of the sensation of gravitoinertial accelerations." Journal of International Advanced Otology. 13(2):154-161, dated 2017.
Review meeting documents RP, Grant Agreement No. 801127, "European Development of Bionic Vestibular Implant For Bilateral Vestibular Dysfunction," Oct. 31, 2019, 97 pages.
Todd et al., "Vestibular receptors contribute to cortical auditory evoked potentials." Hearing Research. Mar. 1, 2014;309:63-74.
Todd, "Evidence for a behavioral significance of saccular acoustic sensitivity in humans," J Acoust Soc Am. Jul. 2001;110(1):380-390. [Abstract only].
Zijlstra et al., "Biofeedback for training balance and mobility tasks in older populations: a systematic review." Journal of neuroengineering and rehabilitation. 7(1):58, 15 pages, Dec. 1, 2010.
"New Concepts in Electrical Stimulation in Vestibular Dysfunction", Audiology & Neurotology, 25: 1-2 (2020).
Sluydts, M. et al., "Electrical Vestibular Stimulation in Humans: A Narrative Review", Audiology Neurotology, 25: 6-24 (2020).
Curthoys, I., "Concepts and Physiological Aspects of the Otolith Organ in Relation to Electrical Stimulation", Audiology Neurotology, 25: 25-34 (2020).
Ramos de Miguel, A. et al., "The Superiority of the Otolith System", Audiology Neurotology, 25: 35-41 (2020).
Manrique-Huarte, R. et al., "Correlation between High-Resolution Computed Tomography Scan Findings and Histological Finds in Human Vestibular End Organs and Surgical Implications", Audiology Neurotology, 25: 42-49 (2020).
Barbara, M. et al., "Early Assessment of Vestibular Function after Unilateral Cochlear Implant Surgery", Audiology Neurotology, 25: 50-59 (2020).
Wolter, N. et al., "BalanCI: Head-Referenced Cochlear Implant Stimulation Improves Balance in Children with Bilateral Cochleovestibular Loss", Audiology Neurotology, 25: 60-71 (2020).
Perez-Fernandez, N. et al., "Bilateral Vestibular Hypofunction in the Time of the Video Head Impulse Test", Audiology Neurotology, 25: 72-78 (2020).
Ramos Macias, A. et al., "Chronic Electrical Stimulation of the Otolith Organ: Preliminary Results in Humans with Bilateral Vestibulopathy and Sensorineural Hearing Loss", Audiology Neurotology, 25: 79-90 (2020).
Starkov, D. et al., "Restoring the High-Frequency Dynamic Visual Acuity with a Vestibular Implant Prototype in Humans", Audiology Neurotology, 25: 91-95 (2020).
Phillips, J. et al., "Interactions between Auditory and Vestibular Modalities during Stimulation with a Combined Vestibular and Cochlear Prosthesis", Audiology Neurotology, 25: 96-108 (2020).

* cited by examiner

BALANCE COMPENSATION

CROSS-REFERENCE TO RELATED APPLICATION

This application claims benefit of European Patent Application Serial No. 20382323.2, filed 21 Apr. 2020, and which application is incorporated herein by reference. A claim of priority is made to the above-disclosed application.

STATEMENT OF FUNDING

The project leading to this application has received funding from the European Union's Horizon 2020 research and innovation programme under grant agreement No 801127.

BACKGROUND

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In an example, there is a method comprising: selecting a recipient having a balance disorder; inhibiting the recipient's vestibular system, and providing a balance compensation output signal to the recipient via one or more non-vestibular sensory channels of the recipient.

In another example, there is a system comprising: a vestibular inhibitor configured to inhibit a recipient's vestibular system, and a stimulator configured to stimulate tissue of the recipient via one or more non-vestibular sensory channels of the recipient based on balance compensation output signals.

In yet another example, there is an apparatus comprising: an implantable stimulation assembly comprising a stimulation set of one or more electrodes configured to stimulate cochlear tissue of a recipient; an implantable inhibition assembly comprising an inhibition set of one or more electrodes configured to stimulate an otolith region or semicircular canals of the recipient; a vestibular inhibitor signal generator configured to provide stimulation signals to the implantable inhibition assembly to inhibit the recipient's vestibular system; and a balance signal generator configured to generate one or more balance compensation output signals to cause stimulation via the implantable stimulation assembly.

BRIEF DESCRIPTION OF THE DRAWINGS

The same number represents the same element or same type of element in all drawings.

DETAILED DESCRIPTION

Figure 1:
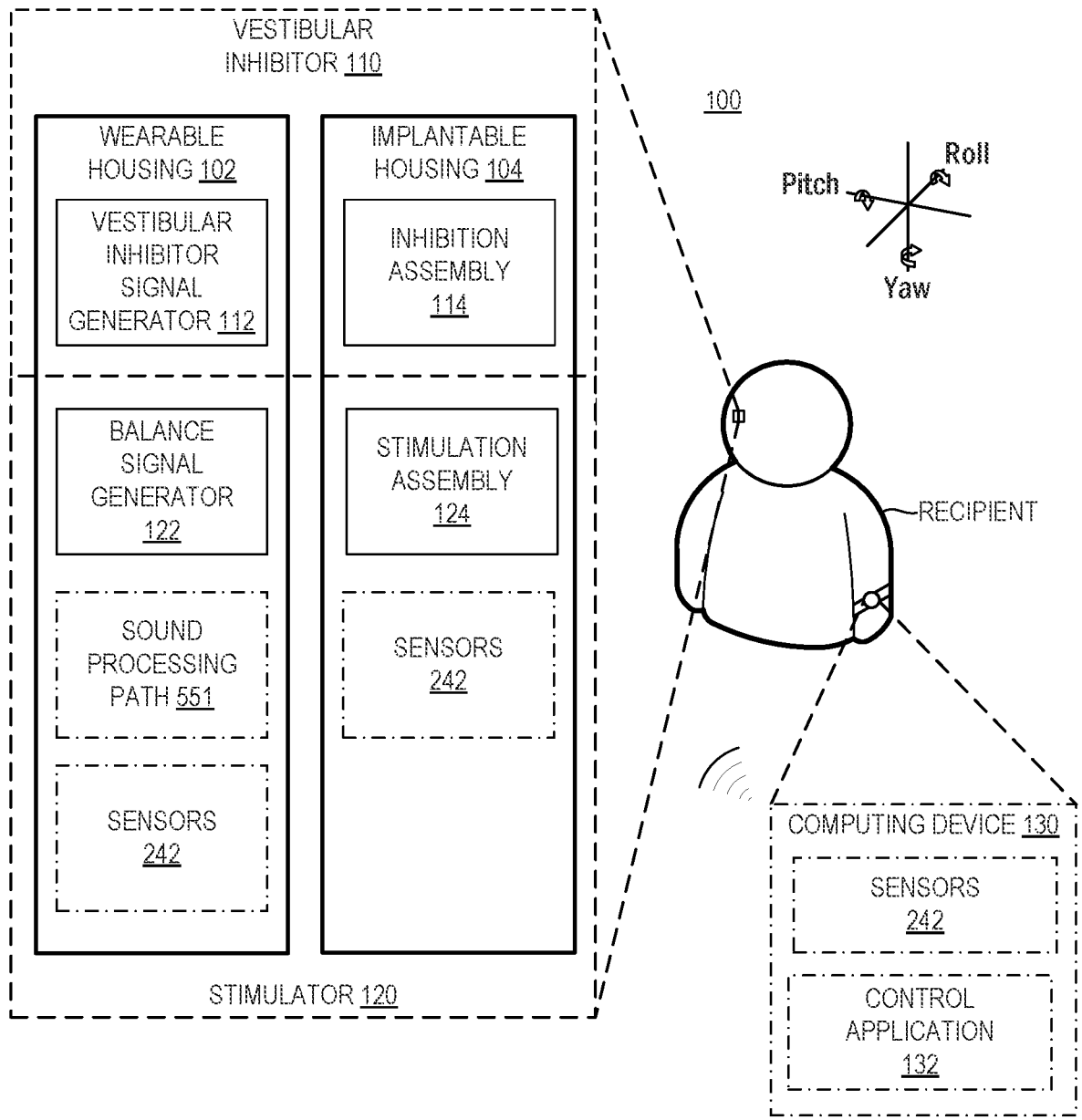
FIG. 1 illustrates an example system for treating a balance dysfunction of a recipient.

Technology disclosed herein includes systems and methods for sensory substitution by suppressing one sensory channel and providing signals via another. In one example, a system suppresses a dysfunctional vestibular system and provides substitute vestibular information via another sensory channel. Dysfunctional balance information from a recipient's vestibular system can be suppressed using electrical stimulation. The electrical stimulation can be provided to the otolith region, semicircular canals, vestibular nerve or another portion of the recipient's vestibular system. Balance information that would normally be provided by a healthy vestibular system (e.g. how the recipient is positioned with respect to gravity, such as rotation along pitch and roll axes) is provided via stimulation of another sensory channel. Such sensor channels can include visual, audible, or tactile sensory channels. For example, audible percepts can be generated via an auditory prosthesis (e.g., a cochlear implant providing electrical stimulation in the recipient's cochlea). By suppressing one sensory channel and providing stimulation via another, one sense can be substituted for another. While described herein primarily in the context of vestibular sensory substitution, sensory substitution can be extended to other sensory systems.

In another aspect there is an architecture for a combined auditory prosthesis and sensory substitution system. In an example, sensory substitution is delivered as perceptible auditory cues that are provided via intracochlear electrodes. The sensory substitution cues can be provided via one or more dedicated intracochlear electrode channels, rather than being superimposed on all hearing channels. In such examples, the remaining electrodes can deliver standard cochlear implant stimulation (e.g., to cause auditory precepts to make up for a dysfunctional auditory system). Balance signals that can substitute for the dysfunctional vestibular system can originate from one or more accelerometers, magnetometers other sensors, or combinations thereof that pass pitch, roll and yaw information to a balance signal generator. The balance signals that substitute for the dysfunctional vestibular system can then be injected into the cochlear stimulation signal processing path in such a manner as to not interfere with (or be interfered by) other signal channels. Thus, while some of the sound processing path can be shared between balance signals and sound input signals (e.g., from a microphone or other sound source), some of the processing path can be exclusive to the balance input signals. In at least some examples, some of the processing path can be exclusive to the sound input signals and some of the processing path can be shared by both the sound input signals and the balance input signals.

The various balance signals that can be used to substitute for a dysfunctional vestibular system include movement or position compared to gravity that is used as an indicator of stability of the recipient. Such a signal can be used to provide information allowing the recipient to quickly recover from stumble or incident of balance failure, which can aid in fall prevention. In another example, gait information is extracted from one or more sensors placed at different locations on the recipient's body (e.g., in a smart watch, phone, gait monitor, step counter, or another device having one or more sensors). Extraction of gait information can be used to predict falls. Fall prediction can be used in combination with fall prevention techniques by, for example, providing balance substitution when gait analysis indicates that there is a risk of falling.

An example system usable to implement one or more examples of this technology is described in FIG. 1.

Example System

FIG. 1 illustrates an example system 100 for treating a balance dysfunction of a recipient. The illustrated system 100 includes a vestibular inhibitor 110 and a stimulator 120.

The vestibular inhibitor 110 is a portion of the system 100 configured to inhibit the recipient's vestibular system. The vestibular inhibitor 110 can include a vestibular inhibitor signal generator 112 and an inhibition assembly 114, which can be disposed in the same or separate housings.

The vestibular inhibitor signal generator 112 can be a component that controls the stimulation provided by the inhibition assembly 114, such as by being or including one or more processors that provide signals. For example, the vestibular inhibitor signal generator 112 can be configured to provide stimulation signals to the inhibition assembly 114.

The inhibition assembly 114 can take any of a variety of forms. The inhibition assembly 114 can include one or more stimulation electrodes. The inhibition assembly 114 can be or include an implantable assembly configured to apply electrical stimulation to an otolith region, semicircular canals, other vestibular tissue of the recipient, or combinations thereof using the one or more electrodes. The electrical stimulation can inhibit the signals provided by the vestibular system to reduce the perception of signals produced by a portion of the vestibular system. For example, where the vestibular system of the recipient is dysfunctional, the stimulation provided by the vestibular inhibitor 110 can be sufficient to reduce or eliminate the perception of dysfunctional signals by the recipient. In some examples, this is achieved by preventing the vestibular system from producing signals or by causing the signals that are produced by the vestibular system to be noisy or otherwise have properties that cause the signals to be disregarded by the recipient.

Additional example implementations of a vestibular stimulator that can act as one or both of the vestibular inhibitor signal generator 112 and the inhibition assembly 114 are described in relation to European Patent Application No. 19382629.4 and European Patent Application No. 19382632.8, both of which were filed on Jul. 24, 2019, and are hereby incorporated by reference in their entirety for any and all purposes.

The stimulator 120 is a portion of the system 100 configured to cause a sensory percept (e.g., audio, visual, or tactile precepts) for the recipient. Such a sensory percept can be used to, for example, provide balance compensation signals to the recipient via one or more non-vestibular sensory channels of the recipient. Balance compensation signals can be signals that cause sensory percepts configured to compensate for a dysfunctional vestibular system. For instance, the balance compensation signals can provide balance information relating to the percepts that would be provided by a normally functioning vestibular system, such as information regarding balance, equilibrium, and orientation in space, among others.

The stimulator 120 can be configured to target one or more non-vestibular sensor channels of the recipient with stimulation to convey balance information. The stimulator 120 can include a balance signal generator 122 and a stimulation assembly 124, disposed in a same or separate housings.

The balance signal generator 122 can be a component configured to generate one or more balance compensation output signals to cause stimulation via the stimulation assembly 124. The balance compensation output signals can be configured to compensate a vestibular deficiency, such as by providing precepts indicative of balance information in a manner that bypasses a defective vestibular system of a recipient.

The stimulation assembly 124 can be a component configured to cause one or more sensory percepts in the recipient to provide the balance information based on the balance compensation output signals. For example, the sensory percepts can provide the balance information to the recipient via one or more non-vestibular sensory channels of the recipient. The one or more sensory channels can include, for example, a visual sensory channel, an auditory sensory channels, a tactile sensory channels, other sensor channels, or combinations thereof. Various characteristics of these sensory channels can be modified to convey different components of balance information. For example, providing balance information regarding rotation about a first axis (e.g., a roll axis) can be performed using a first characteristic, and providing balance information regarding rotation about a second axis (e.g., a pitch axis) can be performed using a second characteristic. In another example, providing balance information regarding rotation about a first axis (e.g., a roll axis) can be performed using a first sensory channel, and providing balance information regarding rotation about a second axis (e.g., a pitch axis) can be performed using a second sensory channel.

Where the sensory channel is a visual sensory channel, the stimulation assembly 124 can be configured to cause the recipient to experience visual percepts that convey the balance information. The balance signal generator 122 can provide signals to the stimulation assembly 124 to vary characteristics of the visual percept to convey the balance information. The visual characteristics can include, for example, characteristics of light provided by a set of one or more lights that make up the stimulation assembly 124 (e.g., LED lights), such as color, brightness, blinking frequency, location, pattern, other characteristics, or combinations thereof. In an example, the stimulation assembly 124 includes a display (e.g., an LCD display) that can show balance information in any of a variety of forms (e.g., a visual diagram or textual description). The stimulator 120 can be configured to provide such information visually by, for example, disposing one or more light emitting elements of the stimulation assembly 124 proximate the recipient's eyes such that the light emitting elements are disposed in the recipient's field of view. The stimulator 120 can be configured as a wearable headset (e.g., shaped like a pair of eyeglasses). In examples, the stimulator 120 can directly stimulate portions of the recipient's visual system, such as with a visual prosthesis. In such an example, the stimulation assembly 124 can be an implantable component configured to provide electrical stimulation to the recipient to cause visual percepts.

Where the sensory channel is a tactile sensory channel, the stimulation assembly 124 can be configured to cause tactile percepts that are indicative of the balance information. In an example, the stimulation assembly 124 can include one or more vibratory actuators that vibrate the recipient's skin to convey the balance information tactilely. The balance signal generator 122 can provide signals to the stimulation assembly 124 to vary characteristics of the tactile percept to convey the balance information. The characteristics modifiable to indicate balance information can include, for example, vibration strength, vibration frequency, and vibration location, among others.

Where the sensory channel is an audio sensory channel, the stimulation assembly 124 can be configured to cause audio percepts in the recipient that are indicative of the balance information. In an example, the stimulation assembly 124 can be a headset with speakers. The stimulator 120 can be a wearable or implantable auditory prosthesis medical device, such as a bone conduction device or a cochlear implant. In such examples, the stimulation assembly 124 can be or include a vibratory bone conduction actuator or an electrode assembly of a cochlear implant. The balance signal generator 122 can provide signals to the stimulation assembly 124 to vary characteristics of the audio percept to convey the balance information. The characteristics modifiable to indicate balance information can include, for example, loudness, pitch, stimulation frequency, location (e.g., left or right side), other characteristics, or combinations thereof. In addition to or instead of tones, the audio percepts can be audio descriptions, such as can be provided by a text-to-speech system describing the balance information.

The balance compensation signals can be generated to cause precepts that convey balance information relating to movement about one or more of pitch, roll, or yaw axes. Rotation about the pitch axis can relate to the recipient's head tilting up and down (e.g., in a nodding motion). Rotation about the roll axis can relate to the recipient's head tilting left or right. Rotation about the yaw axis can relate to the recipient's head rotating left or right. As an example implementation of the stimulator 120 can provide audio signals at a first frequency (e.g., corresponding to the pitch Di) to represent a positive rotation about the roll axis and at a second frequency (e.g., corresponding to the pitch CO to represent a negative rotation about the roll axis. A degree of rotation can be represented by changing a volume of the audio signal provided. For instance, a volume can be approximately 0 dB when the rotation is approximately 0 degrees and can increase to approximately 60 dB as the rotation approaches 90 degrees. As the recipient becomes accustomed to such signals indication rotation, the signals can substitute for a dysfunctional vestibular system of the recipient. In some examples, the stimulator 120 can further include a sound processing path 551. The balance signal generator 122 can be configured to inject balance compensation output signals into the sound processing path 551, such as is described in more detail in relation to FIG. 5 herein. Audible percepts are one of a variety of kinds of ways such information can be provided. The stimulator 120 can take any of a variety of forms.

While the system 100 can be a single-purpose system (e.g., to solely treat balance dysfunctions by inhibiting vestibular organs and providing balance signals). The system can be a multi-purpose system, such as by the stimulator 120 providing sensory compensation for multiple sensory systems of the recipient. For example, in addition to providing compensation for a dysfunctional vestibular system, the stimulator 120 can cause stimulation to compensate for a dysfunctional visual or auditory system of the recipient. In such an example, the balance signal generator 122 can be in addition to a signal generator to treat the sensory defect. For instance, the stimulator 120 can be an auditory prosthesis configured to cause hearing percepts in the recipient that are indicative of the auditory environment around the recipient. Such a stimulator 120 can further include a sound processing path configured to convert an environmental sound input signal into an auditory stimulation signal to cause stimulation via the stimulation assembly 124. The balance signal generator 122 can inject a balance information output signal into the sound processing path to cause a hearing percept in the recipient that is indicative of the balance information.

As described above, the various components of the system 100 can be disposed in same or separate housings. As illustrated, the system 100 can include a wearable housing 102 in which the vestibular inhibitor signal generator 112, balance signal generator 122, and the sound processing path 551 are disposed. The wearable housing 102 can be configured to be worn by the recipient, such as via a headband, magnetic connection, hair clip, or via another technique. As further illustrated, the system 100 can include an implantable housing 104. The implantable housing 104 can at least partially include the inhibition assembly 114 and the stimulation assembly 124. For example, the assemblies 114, 124 can extend from the implantable housing 104. The implantable housing 104 can be constructed from or coated with a biocompatible material. In some examples, the implantable housing 104 further includes one or more of the vestibular inhibitor signal generator 112, the balance signal generator 122, and the sound processing path 551. While the various components can be separated into a wearable housing 102 and an implantable housing 104, in some examples, the components can be disposed entirely in the wearable housing 102 or the implantable housing 104. For example, some implementations can implement the vestibular inhibitor 110 and the stimulator 120 as a totally-implantable device.

As illustrated, there is one stimulator 120 and one vestibular inhibitor 110 disposed on one side of the recipient's head. In other examples, the recipient can have multiple different stimulators 120 and vestibular inhibitors 110. In an example, there is a bi-lateral configuration where there are both left- and right-side vestibular inhibitors 110 and left- and right-side stimulators 120. Such components can be configured to stimulate respective left and right vestibular or other tissue of the recipient. In some examples, the multiple components can cooperate with each other to provide substantially the same or different stimulation. In some examples, the sidedness of the stimulation (e.g., more intense signals on one side rather than the other) can indicate a particular balance state.

As illustrated, some examples of the system 100 can further include one or more sensors 242 disposed in various locations throughout the system 100. The sensors 242 can be, for example, one or more sensors for detecting data used for the balance or gait information, such as accelerometers, gyroscopes, piezoelectric sensors, other sensors, or combinations thereof. Additional example sensors 242 include physiological sensors, such as heartbeat, galvanic skin response sensors, blood pressure sensors, electromyography sensors, other sensors, or combinations thereof. Still further examples of the sensors 242 include microphones and light sensors, among others. The sensors 242 can include components disposed within or connected to (e.g., via wired or wireless connections) the components of the system 100. In some examples, the sensors 242 include software sensors, such as software that obtains data from one or more of the sensors 242 and produces additional data based thereon. For example, a software sensor can be configured to obtain data from one or more gyroscopes and accelerometers to produce gait data regarding the recipient. The gait data can relate to how the recipient is walking, running, or otherwise moving. Such data can describe whether the recipient is limping, lurching, or otherwise has an abnormal gate that can be indicative of a balance issue.

As further illustrated, some examples of the system 100 can further include a computing device 130. The computing device 130 can be a computing device associated with the recipient of the stimulator 120. In many examples, the computing device 130 is a cell phone, tablet, smart watch, step counter, or heart rate monitor, but the computing device 130 can take other forms. Although described primarily in the context of the recipient, the computing device 130 can be a computing device owned or primarily used by a parent or caregiver for the recipient. The computing device 130 can have one or more processors configured to perform operations based on instructions stored in memory of the computing device 130. The computing device can further include one or more interfaces for interacting with a user (e.g., via a touchscreen) or other devices (e.g., a wireless transceiver). In the illustrated example, the computing device 130 includes one or more sensors 242 and a control application 132.

The control application 132 can be a computer program stored as computer-executable instructions in memory of the computing device 130 that, when executed, performs one or more tasks relating to the system 100. The control application 132 can cooperate with one or both of the vestibular inhibitor 110 and the stimulator 120. For instance, the control application 132 can control when and how inhibition is provided by the vestibular inhibitor 110 and when and how signals are provide by the stimulator 120. In some examples, such control of the functioning of components of the system 100 can be performed automatically by the control application 132 or based on input received from a user of the computing device 130. The control application 132 can further provide data from one or more signals from sensors 242 of the computing device 130 to the stimulator 120 for use by the balance signal generator 122. The computing device 130 can connect to one or both of the vestibular inhibitor 110 and the stimulator 120 using, for example, a wireless radiofrequency communication protocol (e.g., BLUETOOTH). The control application 132 can transmit or receive data from one or both of the vestibular inhibitor 110 and the stimulator 120 over such a connection. Where the stimulator 120 includes the sound processing path 551, the control application 132 can be configured to stream audio as input into the sound processing path 551, such as from a microphone of the sensors 242 or an application running on the computing device 130 (e.g., a video or audio application). In other examples, another application running on the computing device 130 can stream audio to the sound processing path 551.

As described above, the components of the system 100 can take any of a variety of forms. An example apparatus that can be used to implement one or both of the vestibular inhibitor 110 and the stimulator 120 is described in FIG. 2.

Example Inhibitor and Stimulator

Figure 2:
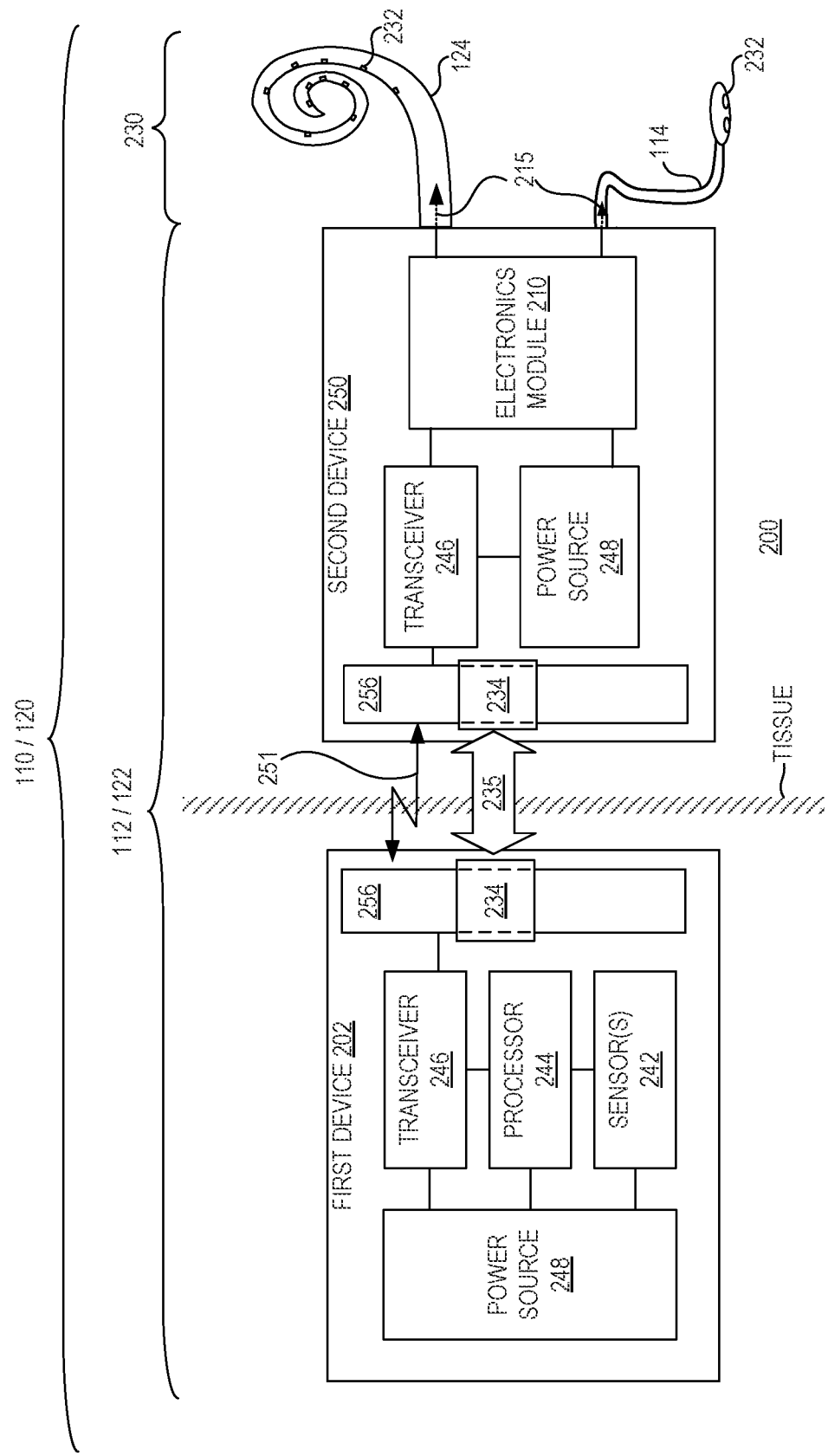
FIG. 2 is a functional block diagram of an example apparatus that be used to implement one or both of a vestibular inhibitor and a stimulator.

FIG. 2 is a functional block diagram of an example apparatus 200 that be used to implement one or both of the vestibular inhibitor 110 and the stimulator 120. In the illustrated example, the apparatus 200 includes a first device 202 acting as an external processor device and a second device 250 acting as an implanted stimulator device. In examples, the second device 250 is an implantable stimulator device configured to be implanted beneath a recipient's tissue (e.g., skin). In examples, the second device 250 includes a biocompatible housing. The first device 202 can be a device configured to couple with (e.g., wirelessly) the second device 250 to provide additional functionality, such as stimulation control signals or charging. While the apparatus 200 is shown as having both implantable and external components, implementations of the apparatus 200 can be entirely external or entirely implantable.

In the illustrated example, the first device 202 includes one or more sensors 242, a processor 244, a transceiver 246, and a power source 248. The one or more sensors 242 can be units configured to produce data based on sensed activities. In an example where the stimulation system 200 is an auditory prosthesis system, the one or more sensors 242 can include sound input sensors, such as a microphone, a telecoil, wireless audio sources (e.g., a BLUETOOTH transceiver), an electrical input for an FM hearing system, and/or another component for receiving sound input. Where the stimulation system 200 is a visual prosthesis system, the one or more sensors 242 can include one or more cameras or other visual sensors. The processor 244 can be a component (e.g., a central processing unit) configured to control stimulation provided by the second device 250. The stimulation can be controlled based on data from the sensor 242, a stimulation schedule, or other data. Where the stimulation system 200 implements an auditory prosthesis, the processor 244 can be configured to convert sound signals received from the sensor(s) 242 (e.g., acting as a sound input unit) into external device signals 251, using, for example, a sound processing path as is described elsewhere herein. The transceiver 246 is a component configured to send signals 251, such as power signals, data signals, other signals, or combinations thereof (e.g., by interleaving the signals). The transceiver 246 can be configured to receive power or data. Stimulation signals can be generated by the processor 244 and transmitted, using the transceiver 246, to the second device 250 for use in providing stimulation.

In the illustrated example, the second device 250 includes an electronics module 210, a stimulator assembly 230, a transceiver 246, a power source 248, and a coil 256. The second device 250 further includes a hermetically sealed, biocompatible housing enclosing one or more of the components.

The electronics module 210 can include one or more other components to provide stimulation. In many examples, the electronics module 210 includes one or more components for receiving a signal and converting the signal into the stimulation signal 215. The electronics module 210 can further include a stimulator unit. The electronics module 210 can generate or control delivery of the stimulation signals 215 to the stimulator assembly 230 to stimulate tissue proximate the stimulation assembly 230. In examples, the electronics module 210 includes one or more processors (e.g., central processing units) coupled to memory components (e.g., flash memory) storing instructions that when executed cause performance of an operation described herein. In examples, the electronics module 210 generates and monitors parameters associated with generating and delivering the stimulus (e.g., output voltage, output current, or line impedance). In examples, the electronics module 210 generates a telemetry signal (e.g., a data signal) that includes telemetry data. The electronics module 210 can send the telemetry signal to the first device 202 or store the telemetry signal in memory for later use or retrieval.

The apparatus 200 can include one or more stimulator assemblies 230 can be one or more components configured to provide stimulation to target tissue. In the illustrated example, there are two stimulator assemblies 230 with one corresponding to the implantable inhibition assembly 114 and the implantable stimulation assembly 124. Further in the illustrated example, the stimulator assemblies 230 are electrode assemblies that includes arrays of electrodes 232 disposed on a lead configured to be inserted into the recipient's cochlea. The stimulator assembly 230 can be configured to deliver stimulation signals 215 (e.g., electrical stimulation signals) generated by the electronics module 210 to the cochlea to cause a hearing percept in the recipient. In some examples, the stimulator assembly 230 is a vibratory actuator disposed inside or outside of a housing of the second device 250 and configured to generate vibrations. The vibratory actuator receives the stimulation signals 215 and, based thereon, generates a mechanical output force in the form of vibrations. The actuator can deliver the vibrations to the skull of the recipient in a manner that produces motion or vibration of the recipient's skull, thereby causing a hearing percept by activating the hair cells in the recipient's cochlea via cochlea fluid motion. In addition or instead, the actuator can deliver the vibrations to cause tactile percepts in the recipient.

The transceivers 246 can be components configured to transcutaneously receive or transmit a signal 251 (e.g., a power signal or a data signal). The transceiver 246 can be a collection of one or more components that form part of a transcutaneous energy or data transfer system to transfer the signal 251 between the first device 202 and the second device 250. Various types of signal transfer, such as electromagnetic, capacitive, and inductive transfer, can be used to usably receive or transmit the signal 251. The transceiver 246 can include or be electrically connected to the coil 256.

The coils 256 can be components configured to receive or transmit a signal 251, typically via an inductive arrangement formed by multiple turns of wire. In examples, in addition to or instead of a coil, other arrangements can be used, such as an antenna or capacitive plates. Magnets 234 can be used to align respective coils 256 of the first device 202 and the second device 250. For example, the coil 256 of the second device 250 can be disposed in relation to (e.g., in a coaxial relationship) with a magnet 234 to facilitate orienting the coil 256 in relation to the coil 256 of the first device 202 via a magnetic connection 235. The coil 256 of the first device 202 can also be disposed in relation to (e.g., in a coaxial relationship with) a magnet 234.

The power source 248 of the respective devices can be configured to provide operational power to other components. The power sources 248 can be or include one or more rechargeable batteries. Power for the batteries can be received from a source and stored in the battery. The power can then be distributed to the other components of the second device 250 as needed for operation.

As should be appreciated, while particular components are described in conjunction with this, technology disclosed herein can be applied in any of a variety of circumstances. The above discussion is not meant to suggest that the disclosed techniques are only suitable for implementation within systems akin to that illustrated in and described with respect to the figure. In general, additional configurations can be used to practice the methods and systems herein and/or some aspects described can be excluded without departing from the methods and systems disclosed herein. For example, while FIG. 2 illustrates a second device 250 being implanted beneath the recipient's tissue, the system 200 can be formed without an implanted component. Instead, for example, the stimulation assemblies 230 can be configured to be used external stimulators can be used.

The various components of the system 100 can cooperate to compensate for a balance dysfunction of a recipient of the system 100. An example process of using the components for such compensation is described in FIG. 3.

Example Process for Compensating a Balance Dysfunction

Figure 3A:
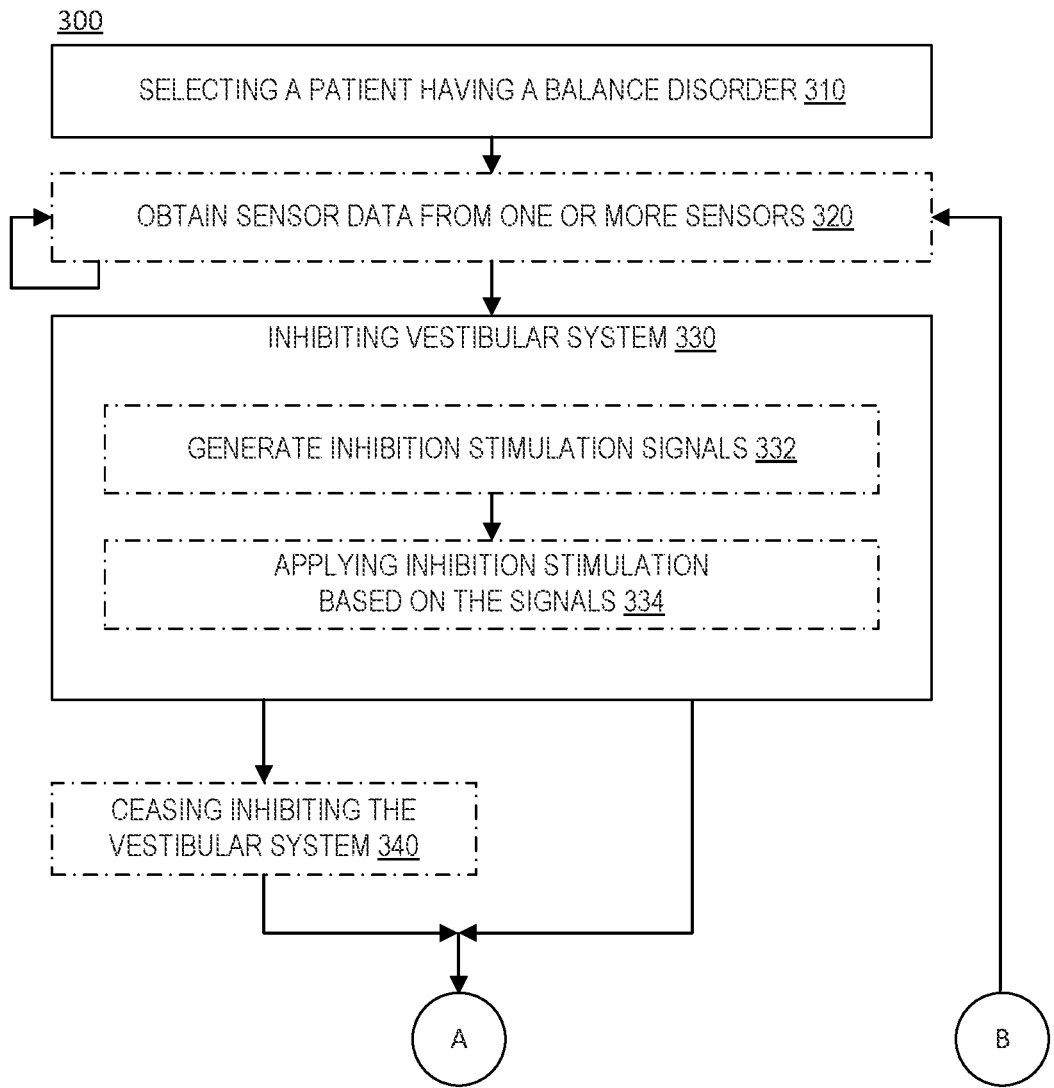
FIG. 3, which is made up of FIG. 3A and FIG. 3B, illustrates an example process for compensating a balance dysfunction.
Figure 3B:
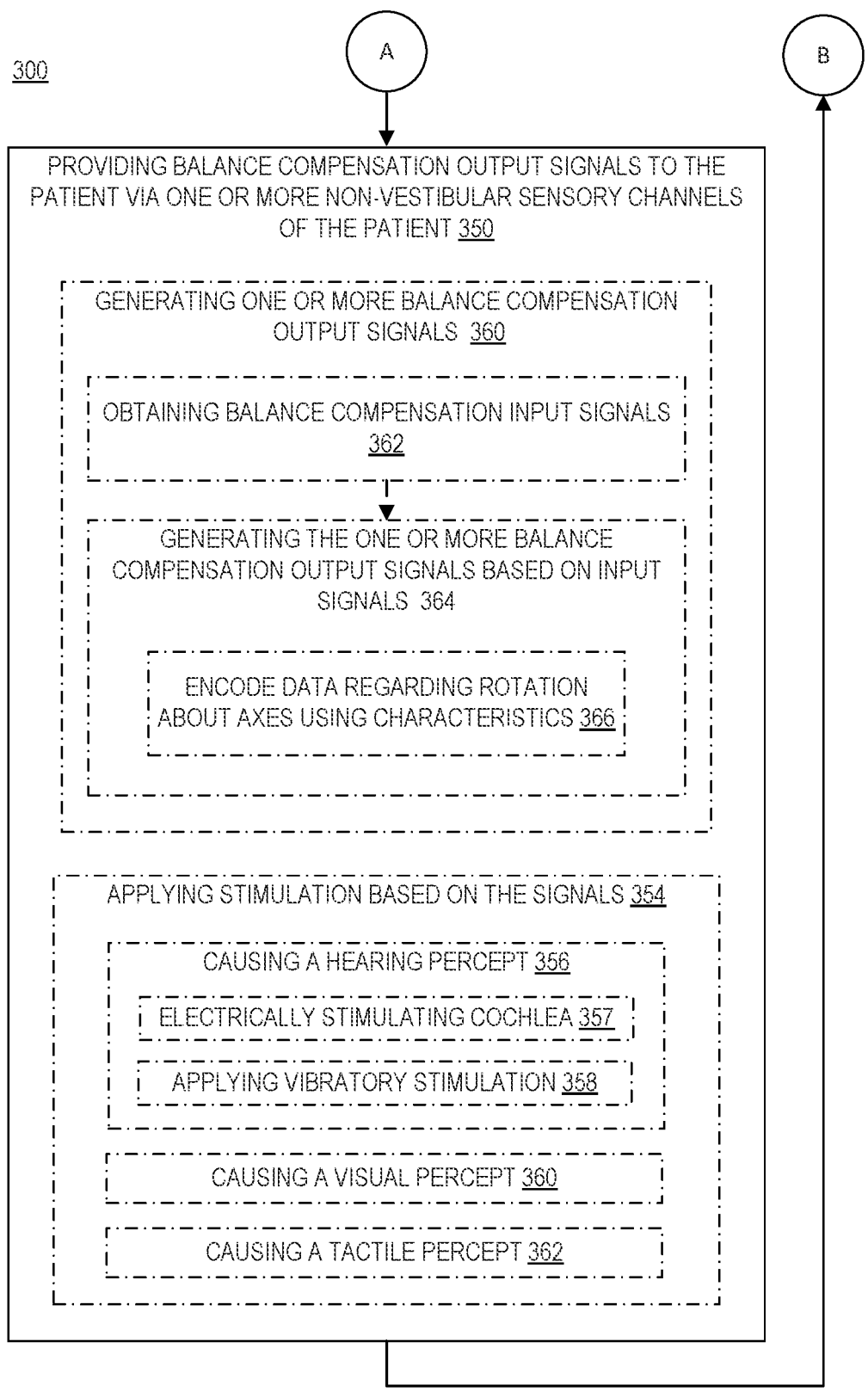

FIG. 3, which is made up of FIG. 3A and FIG. 3B, illustrates an example process 300 for compensating for a balance dysfunction. The process 300 can begin with operation 310.

Operation 310 can include selecting a recipient having a balance disorder. For example, the recipient can be selected as the recipient having or being thought to have one or more symptoms of a balance disorder. The balance disorder can be a dysfunction of the recipient's vestibular system. Following operation 310, the flow of the process 300 can move to operation 320 or operation 330.

Operation 320 can include obtaining data from the one or more sensors 242. For example, one or both of vestibular inhibitor 110 (e.g., the vestibular inhibitor stimulator generator 112 thereof) and the stimulator 120 (e.g., the balance signal generator 122 thereof) can obtain the data. The one or more sensors 242 can be one or more balance sensors that obtain data relating to balance data. Such data can include, for example, accelerometer data, gyroscope data, or magnetometer data. That data can describe rotation around one or more axes, such as pitch, yaw, or roll axes. Obtaining the data from one or more sensors 242 can include obtaining data from physiological sensors, such as heartbeat, galvanic skin response sensors, electromyography sensors, or other sensors. In some examples, one or more of the sensors 242 are disposed remote from the component obtaining the data. The obtaining can include wirelessly obtaining the data from a remote sensor 242. For instance, in an example, the balance signal generator 122 obtains the data from the commuting device 130. Following operation 320, the flow of the process 300 can move to operation 330 or remain at operation 320.

Operation 330 can include inhibiting the recipient's vestibular system. The inhibiting can include the vestibular inhibitor signal generator 112 generating a signal that causes the inhibition assembly 114 to stimulate the recipient's vestibular system in a manner that inhibits dysfunctional signals supplied by the recipient's vestibular system.

In various implementations inhibiting can be substantially constant, intermittent, performed in response to a schedule, or performed based on the sensor data obtained in operation 320. The inhibiting can be controlled automatically or manually. For example, a user interface (e.g., a switch, button, touch screen, or wirelessly connected control) can be provided (e.g., at the computing device 130) to permit the recipient or a caregiver thereof to engage or disengage the inhibition. Such a user interface can also be used to modify an intensity or other parameters of the inhibition being provided.

Where the inhibiting is based on the sensor data, the inhibiting can be activated in response to sensor data passing a threshold. In an example, the inhibiting can be activated responsive to the sensor data indicating balance difficulties by the recipient. Difficulty can be indicated by, for example, detecting movement patterns indicative of balance issues. Such movement patterns can be detected using hard-coded rules, such as decision trees. In other examples, a machine-learning approach is used to determine whether balance difficulties are present. For instance, there can be a machine learning framework (e.g., a neural network) trained to obtain sensory data as input and provide as output an indication whether a balance dysfunction event is occurring. Responsive to the balance dysfunction event occurring, the inhibition can be activated. In some examples, the process 300 can remain at operation 320 until the sensor data passes a particular threshold. For example, the process 300 can remain at operation 320 until the sensor data indicates that the recipient is experiencing a above a threshold amount of vestibular deficiency. For example, the sensor data can indicate that the recipient is falling or about to fall. In response to such an indication, the flow of the process can move to operation 330. In other examples, the flow can remain at operation 320.

In some examples, inhibiting the vestibular system can include deactivating tissue associated with the vestibular system, such as by ablating tissue associated with the vestibular system. In some examples, a pharmacological agent is provided to the recipient that inhibits the vestibular system or a perception of signals provided by the vestibular system. In an example, operation 330 can include operation 332 and operation 334.

Operation 332 includes generating inhibition stimulation signals. The inhibition stimulation signals can be generated using, for example, a processor 244 or an electronics module 210 associated with the inhibitor 110. The generation of the signals can cause the inhibiting to be substantially constant, intermittent, performed in response to a schedule, or performed based on the sensor data. The inhibition stimulation signals can be signals usable to control the delivery of stimulation. For example, the inhibiting can include electrically stimulating the vestibular system with one or more electrodes of the inhibition assembly 114. The stimulation can be configured to mask naturally-occurring signals generated by the vestibular system that can cause abnormal vestibular percepts in the recipient. In some examples, the inhibiting can include delivering stimulation at approximately 500 Hz, approximately 900 HZ, or at less than 1 KHz. Following operation 332, the flow of the process 300 can move to operation 334.

Operation 334 can include applying inhibition stimulation based on the inhibition. stimulation signals. Techniques for applying the stimulation can vary depending on the configuration of the stimulator assembly 230 being used. For example, where the stimulator assembly 230 is an electrode assembly, applying the stimulation can include electrically stimulating the recipient using the stimulator assembly. The stimulation can be delivered to an otolith region, semicircular canals, or other regions of the vestibular system of the recipient to inhibit the vestibular system. In another example, the stimulation is delivered to a vestibular nerve.

Following operation 330, the flow of the process can move to operation 340 or operation 350.

Operation 340 can include ceasing inhibiting the vestibular system. For example, this operation can include ceasing performing operation 330. For instance, electrical or other stimulation of the vestibular system can be stopped. The ceasing can be performed in response to any of a variety of events, such as detecting that the recipient is not walking or otherwise moving. For example, it can be desirable to inhibit the vestibular system while the recipient is moving around and to cease the inhibiting at other times (e.g., when the recipient is sitting or lying down). In some examples, the inhibiting is ceased when the recipient is sleeping (e.g., which can be detected based on a variety of factors, such as a time of day, movement of the recipient, a lack of light detected by a light sensor, other factors, or combinations thereof). In some examples, the inhibiting can occur responsive to detecting that the recipient has an abnormal gait or is falling or about to fall. The inhibiting can cease responsive to determining that such events (e.g., a heightened risk of falling) are no longer occurring. Following operation 340, the flow of the process can move to operation 350.

Operation 350 can include providing balance compensation output signals to the recipient via one or more non-vestibular sensory channels of the recipient. The providing can include providing first balance compensation output signal while inhibiting the recipient's vestibular system. The providing can include providing second balance compensation output signal while the inhibiting is ceased. Operation 350 can include operation 360.

Operation 360 can include generating one or more balance compensation output signals. The balance compensation output signals can be configured for use in compensation of a vestibular deficiency of the recipient. The operation 360 can include generating the balance compensation output signals using the balance signal generator 122. Operation 360 can include operation 362, operation 364, operation 366.

Operation 362 includes obtaining balance compensation input signals 243 from one or more sensors 242. Such balance compensation input signals 243 can include, for example signals relating to rotation about one or more axes. The balance compensation input signals 243 can further include data relating to gait information of the recipient. Following operation 362, the flow of the process can move to operation 364.

Operation 364 includes generating the one or more balance compensation output signals based on balance compensation input. For example, such operation 364 can include operation 366. Operation 366 includes encoding data regarding rotation about one or more axes using one or more characteristics. For example, the operation 366 can include encoding data regarding rotation about first, second, and third axes using respective first, second, and third characteristics. In some examples, the axes are selected from a group consisting of a yaw axis, a roll axis, and a pitch axis. The axes can be with respect to the recipient, such that the rotation about the particular axis provides information about movement of, for example, the recipient's head. The rotation about a first axis can be determined based on, for example compensation input signals obtained from the one or more sensors 242. The characteristics can be characteristics of a percept that is ultimately perceived by a recipient. The encoding can include modifying a signal (e.g., the balance compensation output signals) such that the signal ultimately causes a percept to be detected by the recipient having the characteristic. The characteristics can vary based on a stimulation modality (e.g., tactile precept, audio percept, or visual percept). Further, the chosen stimulation modality itself can be a characteristic that can be used to convey balance information. For instance, where the stimulation modality is audio, such audio characteristics that can be varied to indicate rotation about the various axes can include: loudness, pitch, stimulation frequency, melody, rhythm, location (e.g., left or right side), stereo effect (e.g., a relative loudness or other difference between playback on left or right sides), other characteristics, or combinations thereof. Further, the same characteristic can be used to indicate information regarding rotation about multiple axes.

In an example, rotation about first and second axes is encoded using pitch and encoding an extent of the rotation about the axes using volume. For instance, as a recipient rotates their head about a roll axis, a tone having a first pitch can be played at a first volume. As the recipient continues to rotate their head further, the first volume can increase while the pitch remains the same. In addition, as the recipient rotates their head about a pitch axis, a tone having a second pitch can be played at a second volume. As the recipient continues to rotate their head further, the second volume can increase while the second pitch remains the same. The two tones can be played substantially simultaneously to each other. In some examples, negative or positive rotation angles can be encoded based on which side of a head the sound is played. In some examples, operation 350 can include operation 354.

Operation 354 can include applying stimulation based on the balance compensation output signals. Applying the stimulation can include generating electrical, vibratory, visual, or other kinds of stimulation based on the signal, such as is described herein. Such stimulation can be configured to provide balance compensation. In some examples, operation 354 can include one or more of operation 356, operation 360, and operation 362.

Operation 356 can include causing a hearing percept. Causing a hearing percept can include stimulating the recipient's auditory system so the recipient perceives an audio event. In some examples, operation 356 can include operation 357, which includes electrically stimulating a cochlea of the recipient. For example, the cochlear can be stimulated with one or more intracochlear electrodes. An example of a cochlear implant with which hearing percepts can be caused is described in FIG. 4. In some examples, operation 356 can include operation 358. Operation 358 can include applying vibratory stimulation. The vibratory stimulation can include, for example, causing bone-conducted or air-conducted vibrations, such as from a bone conduction apparatus or consumer audio product, respectively. Such vibrations can cause an auditory precept to be experienced by the recipient.

Operation 360 can include causing a visual percept. Causing a visual percept can include stimulating the recipient's visual system so that the recipient perceives a visual event. In some examples, operation 360 can include activating LEDs (Light Emitting Diodes) or an LCD (Liquid Crystal Display) to cause the visual percept. In other examples, operation 360 can include directly stimulating a recipients visual sensory system via electrical or other stimulation.

Operation 362 can include causing a tactile percept. Causing a tactile percept can include causing one or more vibratory actuators to vibrate the recipient's skin to tactilely convey balance information.

Following operation 350, the flow of the process 300 can return to operation 320 or operation 330.

Example Implementation

Figure 4:
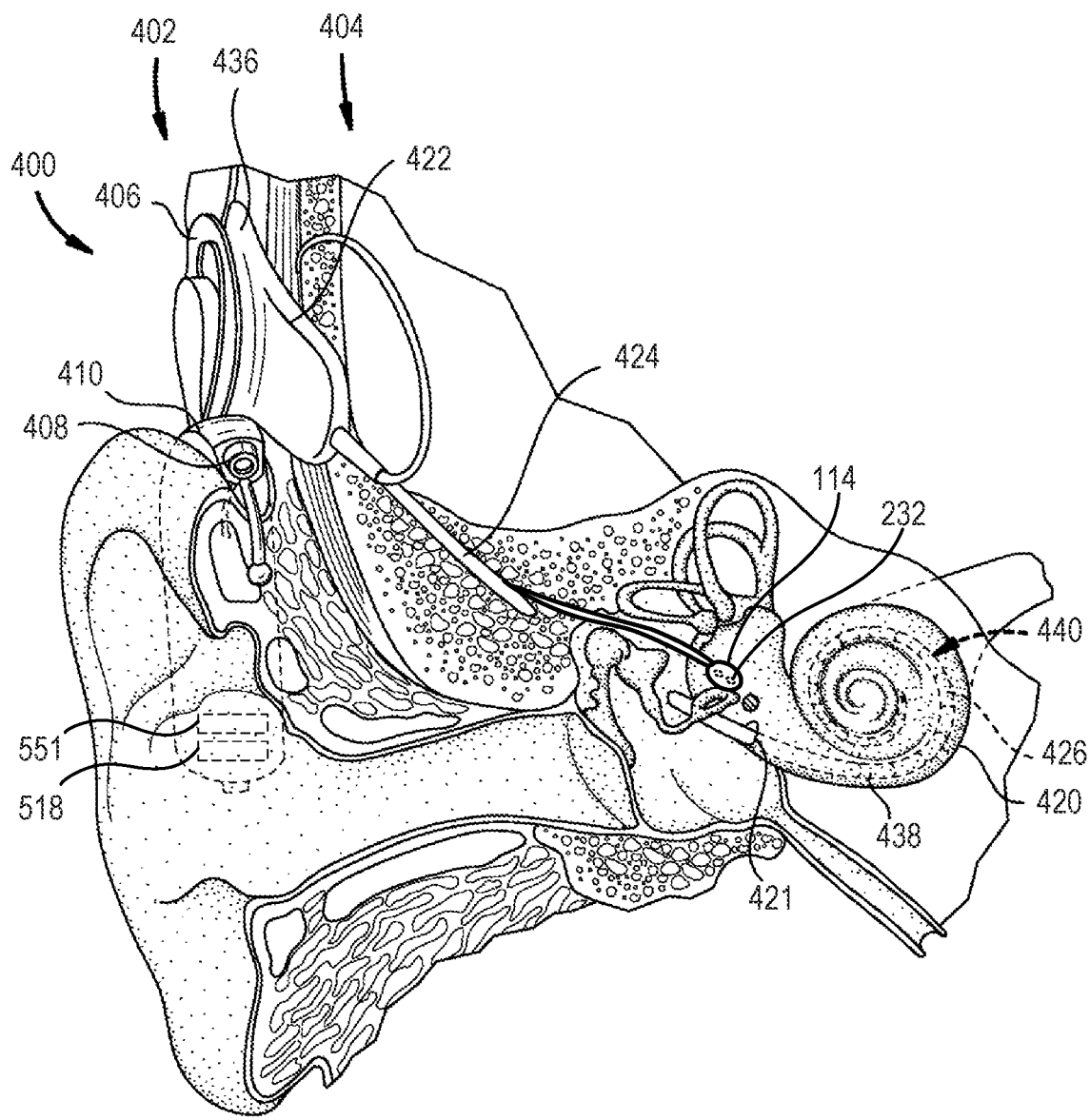
FIG. 4 is schematic diagram of an exemplary cochlear implant with which examples herein can be implemented

FIG. 4 is schematic diagram of a cochlear implant 400 with which examples herein can be implemented. The cochlear implant 400 includes an external component 402. The external component 402 can be directly or indirectly attached to the body of the recipient and comprises a sound processor 410 (which can correspond to the first device 202), an external coil 406 (which can correspond to coils 256). In the illustrated example, the external coil 406 is remote from a main housing of the sound processor 410, and the external coil 406 is connected to the sound processor 410 via a cable 434. The sound processor 410 can be, for example, a behind-the-ear (BTE) sound processing unit, a body-worn sound processing unit, a button sound processing unit, etc.

The example cochlear implant 400 is shown as including an implantable component 404. The implantable component includes an implant body 422, a lead region 424, and an elongate intra-cochlear stimulating assembly 426. The implant body 422 generally comprises a hermetically-sealed housing in which an internal transceiver (e.g., transceiver 246) and a stimulator unit (as a part of electronics module 210) are disposed. The implant body 422 also includes a coil 436 that can be generally external to the housing, but which can be connected to the transceiver via a hermetic feedthrough. The coil 256 can be a wire antenna coil comprised of multiple turns of electrically insulated single-strand or multi-strand platinum or gold wire. The electrical insulation of the coil 256 can be provided by a flexible molding (e.g., silicone molding).

The elongate stimulating assembly 426 (e.g., corresponding to the assembly 124) is configured to be at least partially implanted in the recipient's cochlea 420 and includes a plurality of longitudinally spaced intra-cochlear electrical stimulating electrodes 438 (e.g., electrodes 232) that collectively form a contact array 440. In certain arrangements, the contact array 440 can include other types of stimulating contacts, such as optical stimulating contacts or vibrational portions, in addition to the electrodes 438. The stimulating assembly 426 extends through an opening 421 in the cochlea (e.g., cochleostomy, the round window, etc.) and has a proximal end connected to the stimulator unit via lead region 424 and a hermetic feedthrough. The lead region 424 includes a plurality of conductors (e.g., wires) that electrically couple the electrodes 438 to the stimulator unit.

The cochlear implant 400 further includes the implantable inhibition assembly 114 extending from the lead region 424. As illustrated, the implantable inhibition assembly 114 includes one or more of the electrodes 232 disposed proximate vestibular anatomy. The electrodes 232 can be disposed in vestibular anatomy.

Returning to external component 402, the sound source 408 is a component configured to detect/receive sound signals and to generate electrical signals therefrom. These signals are representative of the detected sound signals. The sound processor can execute sound processing and coding to convert the input signals generated by the sound source 408 into output data signals that represent electrical stimulation signals for delivery to the recipient. In some examples, the sound source 408 is a microphone. In other examples, the sound source 408 is a wireless data receiver configured to obtain, for example, audio data over a wireless transmission protocol, such as via an FM signal or BLUETOOTH.

Signals generated by the processor 244 can be transcutaneously transferred to the cochlear implant 400 the coil 256. For example, the external coil 256 can transmit power and coded data signals to the implantable coil 256. In certain examples, the external coil 256 transmits the signals to the implantable coil 256 via a radio frequency (RF) link. However, various other types of energy transfer, such as infrared (IR), electromagnetic, capacitive and inductive transfer, can be used to transfer the power and/or data from an external component to a cochlear implant.

The coded data signals received at implantable coil 256 are provided to the transceiver 246 and forwarded to the electronics module 210. The electronics module 210 can be configured to use the coded data signals to generate stimulation signals (e.g., current signals) for delivery to the recipient's cochlea via one or more of the electrodes 232. In this way, the cochlear implant 400 stimulates the recipient's auditory nerve cells in a manner that causes hearing percepts, such that the recipient perceives the received sound signals by bypassing absent or defective hair cells that normally transduce acoustic vibrations into neural activity.

The external component 402 or a component connected to the external component can include the balance signal generator 122 as part of a balance signal system 518. As described further below, the balance signal system 518 can be configured to generate one or more balance compensation output signals configured to compensate a vestibular deficiency. The balance compensation output signals can be injected into a sound processing path 551 of the sound processor 410 to cause hearing percepts in the recipient. An example of such a sound processing path 551 and injection of balance compensation output signals is described in FIG. 5.

Example Sound Processing Path Injection

Figure 5:
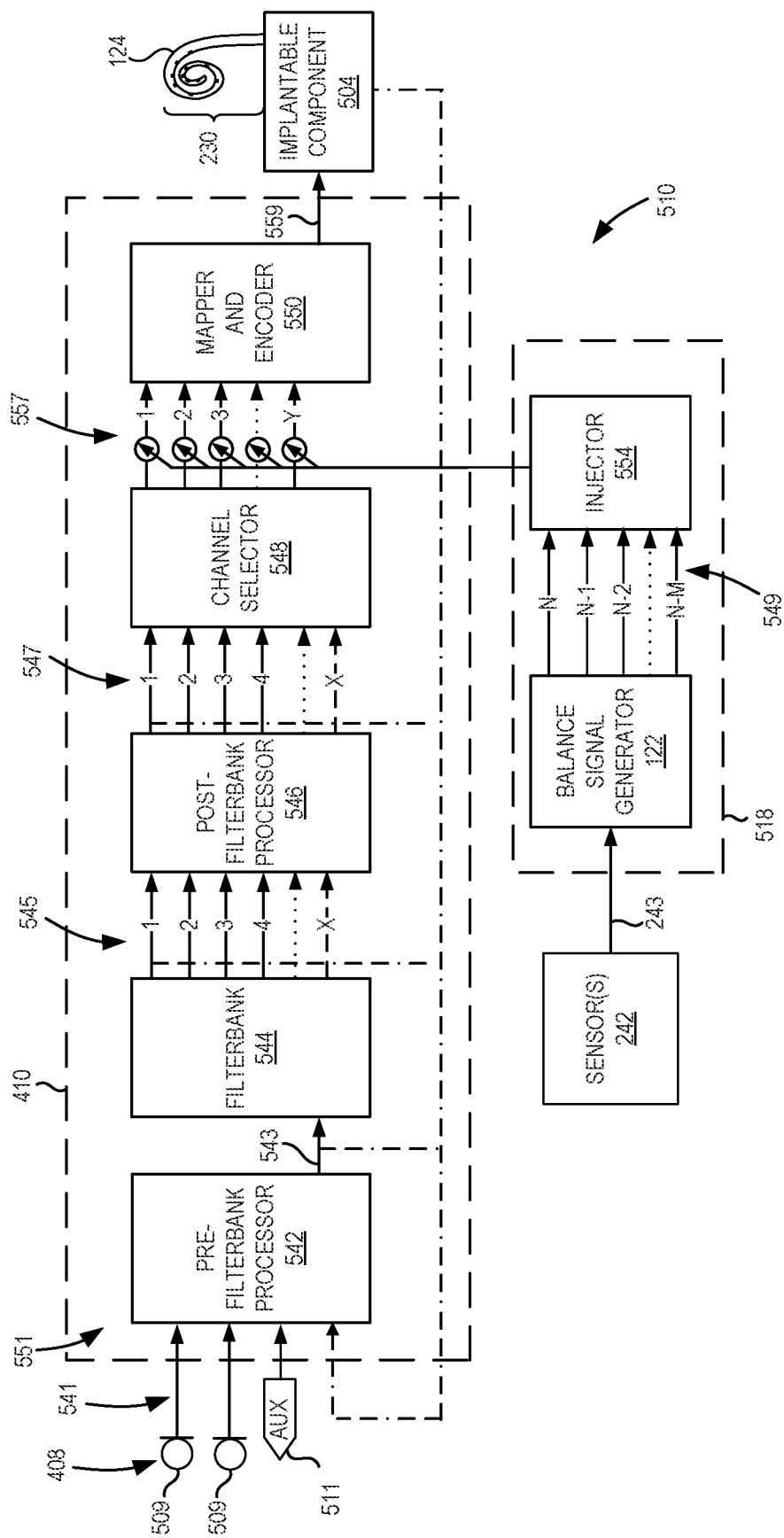
FIG. 5 is a schematic diagram illustrating example arrangements for a sound processor and a balance signal system forming part of a sound processing unit of a cochlear implant in accordance with embodiments presented herein.

FIG. 5 is a schematic diagram illustrating example arrangements for a sound processor 410 and a balance signal system 518 forming part of a system 510 of a cochlear implant in accordance with embodiments presented herein. The illustrated sound processor 410 comprises a pre-filterbank processor 542, a filterbank 544, a post-filterbank processor 546, a channel selector 548, and a channel mapper 550 that collectively form the sound processing path 551 that is configured to convert one or more sound input signals 541 into one or more sound processing path output signals 559 for use in causing a hearing percept in a recipient. The components of the sound processing path 551 (e.g., components 542, 544, 546, 548, and 550) can be modifiers configured to modify the sound input signal 541. The sound processing path output signals 559 that results from the sound processing path 551 can be used in generating electrical stimulation signals for delivery to the recipient to evoke perception of the received sound signals and other data injected into the sound processing path 551. In the illustrated example, the sound processing path 551 begins at the pre-filterbank processing operations of the pre-filterbank processor 542 and sequentially moves through the filterbank operations performed at filterbank 544, the operations performed at the post-filterbank processor 546, the channel selecting operations of the channel selector 548, and terminates at the channel mapping operations performed at channel mapper 550. In other examples, the sound processing path 551 can have more or fewer operations and components, as well as other arrangements of components in parallel, branching, other arrangements, or combinations thereof.

As shown, multiple sound sources 408, such as one or more microphones 509 and one or more auxiliary inputs 511 (e.g., audio input ports, cable ports, telecoils, a wireless transceiver, etc.) receive/detect sound signals which are then provided to the pre-filterbank processor 542. If not already in an electrical form, sound sources 408 convert the sound signals into an electrical form for use by the pre-filterbank processor 542, such as via an analog-to-digital converter. Sound input signal 541 are provided to the pre-filterbank processor 542 (e.g., in the form of electrical input signals). For ease of understanding, the term "sound input signal" 541 can be used to refer to not just the signals as received form the sound sources 408 but also such signals as they are transformed, converted, or otherwise processed through the sound processing path. For instance, sound input signals 541 can be used to refer to pre-filtered input signal 543, hearing signal components 545, processed channelized signals 547, and selected channelized signals 557, unless otherwise noted.

The pre-filterbank processor 542 can be a component configured to, as needed, combine the electrical input signals received from the sound sources 408 and prepare those signals for subsequent processing. The pre-filterbank processor 542 then generates a pre-filtered input signal 543 that is provided to the filterbank 544. The pre-filterbank processor 542 can create the pre-filtered input signal 543 via any of a variety of combining operations. The pre-filtered input signal 543 represents the collective sound signals received at the sound sources 408 at a given point in time.

The filterbank 544 uses the pre-filtered input signal 543 to generate a suitable set of bandwidth limited channels, or frequency bins, that each includes a spectral component of the received sound signals that are to be used for subsequent sound processing. The filterbank 544 can be implemented as a plurality of band-pass filters that separate the pre-filtered input signal 543 into multiple components, each component carrying frequency sub-band (e.g., a single frequency) of the original signal (e.g., frequency components of the received sounds signal as included in pre-filtered input signal 543). For example, the filterbank 544 can be or implement a plurality of band-pass filters configured to convert a sound input signal 541 into a signal having a plurality of hearing signal components that each correspond to one of a set of two or more channels created by the filterbank 544.

The channels created by the filterbank 544 can be referred to as sound processing channels, and the sound signal components within each of the sound processing channels are sometimes referred to herein in as channelized signals. The channelized signals created by the filterbank 544 can be adjusted or modified as the signals pass through the sound processing path 551. As such, the channelized signals can be referred to differently at different stages of the sound processing path 551. Reference herein to a channelized signal can refer to the spectral component of the received sound signals at any point within the sound processing path 551 (e.g., pre-processed, processed, or selected).

At the output of the filterbank 544, the channelized signals are initially referred to herein as hearing signal components 545. As illustrated, there are x channels defined by the filterbank. The value of x can depend on a number of different factors, such as implant design, number of active electrodes, coding strategy, recipient preferences, other factors, and combinations thereof. In certain arrangements, twenty-two channelized signals are created, thus the sound processor 410 would be said to have twenty-two channels.

In many examples, the sound input signals 541 and the pre-filtered input signal 543 are time domain signals (e.g., processing at pre-filterbank processor 542 occurs in the time domain). However, the filterbank 544 can operate to deviate from the time domain and, instead, create a channelized domain in which further sound processing operations are performed. As used herein, the channel domain refers to a signal domain formed by a plurality of amplitudes at various frequency sub-bands. In certain embodiments, the filterbank 544 passes through amplitude information, but not phase information, for each of the x channels. This can be due to methods of envelope estimation that can be used in each channel, such as half wave rectification (HWR), low pass filtering (LPF), quadrature envelope estimation, or Hilbert envelope estimation methods, other techniques, or combinations thereof. As such, the channelized or band-pass filtered signals can be referred to as phase-free signals. In other examples, both phase and amplitude information can be retained for subsequent processing.

In embodiments in which the band-pass filtering operations eliminate the phase information (e.g., generate phase-free signals), the channel domain can be viewed as distinguishable from the frequency domain because signals within the channel domain cannot be precisely converted back to the time domain. That is, due to the removal of the phase information in certain embodiments, the phase-free channelized signals in the channel domain are not exactly convertible back to the time domain.

The sound processing path 551 also includes a post-filterbank processor 546. The post-filterbank processor 546 is a component that can be configured to perform a number of sound processing operations on the plurality of hearing signal components 545. These sound processing operations include, for example gain adjustments (e.g., multichannel gain control), noise reduction operations, or signal enhancement operations (e.g., speech enhancement, wind reduction), other operations, or combinations thereof, in one or more of the channels. Noise reduction can include processing operations that identify unwanted components of a signal (e.g., noise components), and then subsequently reduce the presence of these unwanted components. Signal enhancement can refer to processing operations that identify the target signals (e.g., speech or music) and then subsequently increase the presence of these target signal components. Speech enhancement is a particular type of signal enhancement. After performing the sound processing operations, the post-filterbank processor 546 outputs a plurality of processed channelized signals 547. The plurality of processed channelized signals 547 can be transmitted to the channel selector 548.

The channel selector 548 can be a component that selects a subset of y channels of the x processed channelized signals 547 for use in generation of stimulation for delivery to a recipient. For example, the channels input into the channel selector 548 are reduced from x channels toy channels. In one specific example, they largest amplitude channels (maxima) from the x available channels is made, with x and y being programmable during cochlear implant fitting or operation. Different channel selection methods can be used and need not be limited to maxima selection. The signals selected at channel selector 548 are represented as selected channelized signals 557 or, more simply, selected signals.

The illustrated sound processing path 551 also includes a channel mapper 550. The channel mapper 550 can be configured to map the amplitudes of the selected signals 557 into a set of stimulation commands that represent the attributes of stimulation signals (current signals) that are to be delivered to the recipient so as to evoke perception of the received sound signals. This channel mapping can include, for example, threshold and comfort level mapping, dynamic range adjustments (e.g., compression), volume adjustments, etc., and can encompass sequential and/or simultaneous stimulation paradigms.

In the illustrated example, the set of stimulation commands that represent the stimulation signals are encoded for transcutaneous transmission (e.g., via an RF link) to an implantable component 504. This encoding can be performed at channel mapper 550. As such, channel mapper 550 is sometimes referred to herein as a channel mapping and encoding module and operates as an output block configured to convert the plurality of channelized signals into a plurality of sound processing path output signals 559.

As illustrated, the filterbank 544, the post-filterbank processor 546, the channel selector 548, and the channel mapper 550 collectively form a sound processing path 551 that converts the one or more received sound signals into one or more output signals for use in compensation of a hearing loss of a recipient of the cochlear implant. In other words, the sound processing path 551 extends from the filterbank 544 to the channel mapper 550. The output signals 559 generated by the sound processor 410 comprise a plurality of encoded signals for delivery to the implantable component 504.

The sound processing path 551 can include other components. In addition to or instead of the components described herein. For example, the sound processing path 551 can include adaptive dynamic range optimization components, automatic gain control components, channel combiner components, mixing components, fast Fourier transform components, level detection components, beamforming components, windowing components, calibration filtering components, pre-emphasis components, other components, and combinations thereof.

Additional examples of components and techniques that can be used with the sound processing path 551 to modify the sound input signal 541 are described in U.S. Pat. Nos. 9,473,852 and 9,338,567, which are both incorporated herein by reference for any and all purposes.

As further shown in FIG. 5, a balance signal system 518 can operate with the sound processor 410. In the illustrated example, the balance signal system 518 includes a balance signal generator 122 and an injector 554. The balance signal generator 122 is configured to generate a balance compensation output signal 549. The balance compensation output signal 549 generated by the balance signal generator 122 can be channelized by being formed by a plurality of discrete amplitudes at different frequency sub-bands that each correspond to a channel (e.g., a specific frequency sub-band) of the sound processing path 551. For example, balance signal generator 122 can be configured to generate channelized balance compensation output signal having a plurality of balance compensation signal components that each correspond to one of a first subset of N–M channels. In FIG. 5, the balance compensation output signals 549 can include frequency-limited components or full-band components. In other examples, the balance compensation output signal is not channelized. Such an unchanneled signal can be provided into the sound processing path 551 prior to the filterbank 544, whereby the balance compensation output signal is channelized.

The balance signal generator 122 can receive or obtain balance compensation input signals 243 from one or more of the sensors 242. The balance signal generator 122 can use the balance compensation input signals 243 to generate the balance compensation output signal 549.

As noted, the balance signal system 518 also comprises an injector 554. The injector 554 can be configured to inject the balance compensation output signal 549 into the sound processing channels of the sound processing path 551. For example, one or more components of the balance compensation output signal 549 are combined with, or otherwise applied to, channelized signals in a corresponding sound processing channel (e.g., the components of the balance compensation output signal are separately combined with separate channelized signals). In another example, the injector 554 injects the balance compensation output signal 549 to a pre-channelized signal. As a result, the balance compensation output signal 549 forms part of the one or more sound processing path output signals generated by the sound processor 410 for use in compensation of a hearing loss of a recipient of the cochlear implant 400. The injection of the balance compensation output signal 549 into the sound processing channels of the sound processing path 551 is generally shown at the illustrated injection points 556.

Injection of the balance compensation output signal 549 into one or more sound processing channels can occur in any of a variety of ways, such as: weighted or unweighted summation, weighted or unweighted addition, weighted or unweighted superposition, gated selective injection, rules-based selective injection (e.g., injection only occurs if the channel level satisfies a threshold, such as a masker signal level or a post-filterbank processor output level), random injection, or stochastic injection, other techniques, or combinations thereof. The injection of the balance compensation output signal into one or more of the sound processing channels can also be further controlled by time-based rules, such as: simultaneous injection into two or more channels, round robin channel injection, multiplexed selection of channels for injection, random selection, occasional selection of channels for injection, other techniques or combinations thereof. In some examples, the injection completely replaces (e.g., overwrites) the sound signal that was on the channel prior to injection.

The location at which the balance compensation output signal 549 is injected into the sound processing path 551 can vary. For example, the balance compensation output signals 549 can be injected at a location in the sound processing path after any noise reduction or signal enhancement operations are completed at post-filterbank processor 546, but before channel selection at channel selector 548. In such an example, the channel selection is based on the combination of the processed channelized signals 547 and the balance compensation output signal 549. In other examples, the balance compensation output signal 549 is injected after the channel selector 548 operation is performed. In some examples, certain channels can be treated differently than other channels. For example, a certain subset of the x channels can be set to always be selected by the channel selector 548. For instance, where the balance compensation output signal 549 is injected prior to the channel selector 548, the channel selector 548 can be configured such that the balance compensation output signal 549 is present in they channels after selection.

In the illustrated example, the balance compensation output signal is injected into all of the sound processing channels. In the illustrated example, there are x sound processing channels and N−M balance signal channels. In some examples, channels N through M are dedicated balance signal channels that are not used to carry signals based on the sound input. In some examples, N−M<x. The balance compensation output signal 549 can be channelized (e.g., by the balance signal generator 122 or the filterbank 544) into having a plurality of balance compensation signal components that each correspond to one of a first subset of N−M (e.g., where N−M>1) channels. And the filterbank 544 can be configured to convert the sound input signal 541 into a signal having a plurality of hearing signal components 545 that each correspond to one of a second subset of X channels (e.g., where X>1). The resulting first and second subsets can be disjoint, intersecting, or identical.

In the illustrated example, the injector 554 is configured to inject the balance compensation output signal 549 into the sound processing path 551 between the post-filterbank processor 546 and the channel selector 548. In other words, the injection occurs after the noise reduction, signal enhancement, gain adjustment, and other sound processing operations that have the potential to affect the success of the balance stimulation in some unintended manner, but before a channel selection process. The channel selection process at channel selector 548 is configured to select, according to one or more selection rules, which of the Y processed channelized signals 547, when combined with the balance compensation output signal 549, should be used for hearing compensation.

Balance compensation output signals 549 can have a variety of different number of channels (e.g., more or less than 22 channels is possible). As illustrated, there are N−M channels for the balance signal generator 122. The balance compensation output signals 549 need not be present across an entire spectrum of audible frequencies able to be produced by the system. Instead, the a relatively smaller number of hearing frequencies can be targeted for use in causing percepts representative of balance compensation output signals 549. Thus, in certain examples, there can only be a small number of channels (e.g., one or two channels) used for providing balance compensation output signals 549. The low number of channels can facilitate the recipient associating the particular frequencies produced by those channels as being particular to balance compensation signals rather than general hearing. The channels used for balance compensation output signals 549 being dedicated can further contribute to such an association. In other examples, there can be many more channels used for balance compensation output signals 549 and such channels can be shared with environmental audio signals.

As noted, FIG. 5 illustrates an embodiment in which the injection points 556 for the balance compensation output signal 549 is between the post-filterbank processor 546 and the channel selector 548. However, it is to be appreciated that a balance compensation output signal can be injected into other locations/points of the sound processing path 551 subsequent to noise reduction, signal enhancement, gain adjustment, and other sound processing operations that have the potential to affect the success of the balance compensation in some unintended manner.

Figure 6:
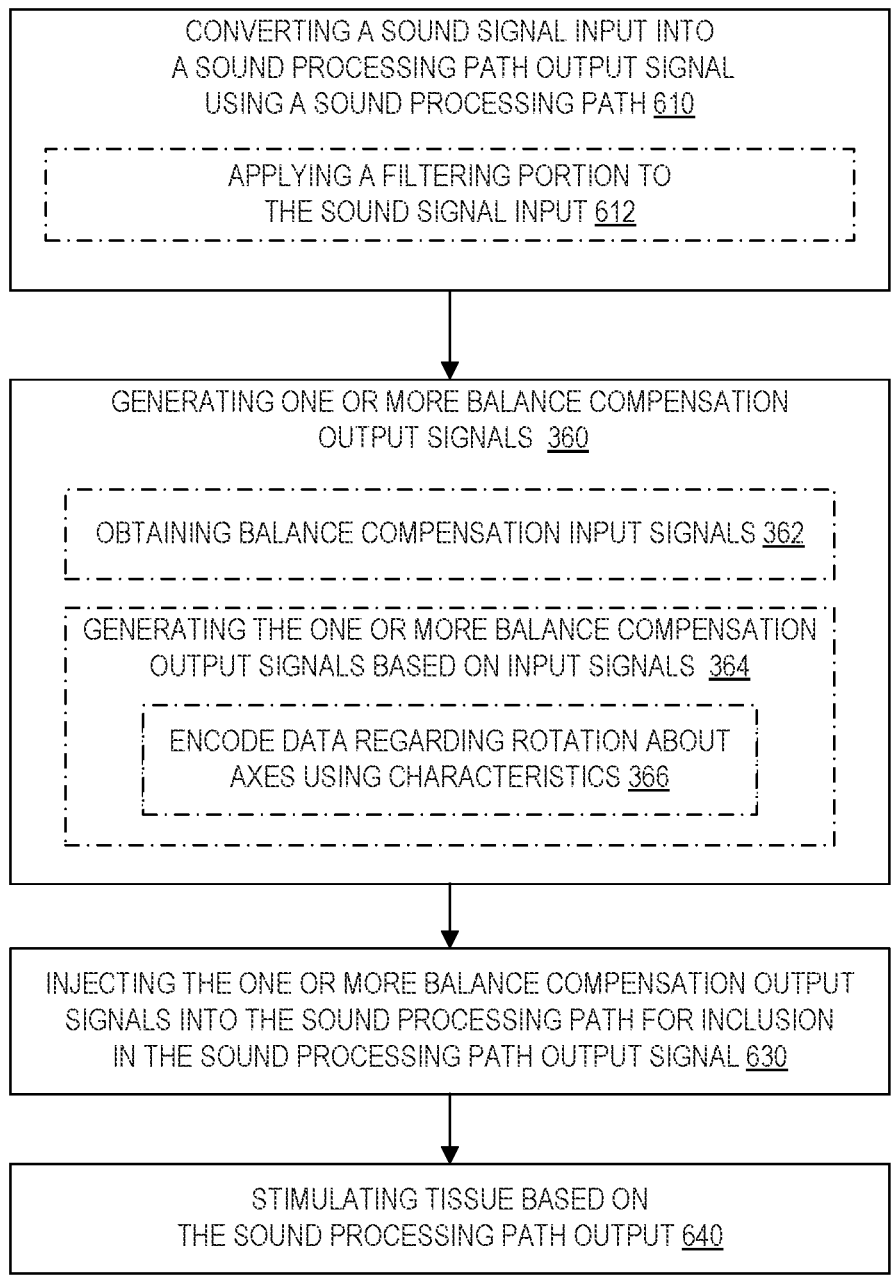
FIG. 6 illustrates an example process for compensating for a balance dysfunction.

An example process for compensating for a balance dysfunction that can be used with the implemented using the components of FIG. 4 and FIG. 5 (among other components), is described in relation to FIG. 6.

Example Method

FIG. 6 illustrates an example process 600 for compensating a balance dysfunction. The process 600 can begin with operation 610.

Operation 610 includes converting a sound input signal 541 into a sound processing path output signals 559. This operation 610 can include obtaining the sound input signal 541 from one or more sound sources 408. For example, the operation 610 can include obtaining the sound input signal from one or more sensors 242 selected from the group consisting of: microphones, telecoils, and wireless audio sources. The converting can include processing the sound input signal 541 using one or more components of the sound input signal 541, such as a pre-filterbank processor, a filterbank 544, a post-filterbank processor 546, a channel selector 548, a mapper 550, and an encoder 550, among other components. In some examples, the operation 610 includes operation 612.

The operation 612 includes applying a filtering portion of the sound processing path 551 to the sound input signal 541. For instance applying the filtering portion can include processing the sound input signal 541 using the filterbank 544. As described above, processing with the filterbank 544 can include applying one or more band-pass filters to separate the sound input signal 541 into multiple components, each one carrying a single frequency sub-band of the original sound input signal 541. In another example, applying the filtering portion can include processing the sound input signal 541 using the post-filterbank processor 546. For instance, as described above, processing with the post-filterbank processor 546 can include: adjusting gain, reducing noise, enhancing particular portions of the sound input signal 541 (e.g., enhancing a speech portion of the sound input signal 541, reducing a wind portion of the sound input signal 541), other operations, or combinations thereof.

The operation 612 can include applying a channelizing portion of the sound processing path 551 to the sound input signal 541. For example, the channelizing portion can be the filterbank 544 and the channelizing can include forming one or more channels from the sound input signal 541.

Following operation 610, the flow of the process 600 can move to operation 360, which as described above in relation to FIG. 3, can include generating one or more balance compensation output signals 549. The balance compensation output signals 549 can be can be channelized. During performance of the process 600, following operation 360, the flow of the process 600 can move to operation 630.

Operation 630 can include injecting the one or more balance compensation output signals 549 into the sound processing path 551 for ultimate inclusion in the sound processing path output signal. The operation 630 can be performed using the injector 554. For example, the injector 554 can be configured to perform operation 630. As a result of the injecting, the sound processing path output signals 559 is based on the one or more injected balance compensation output signals 549. In an example, the balance compensation output signals 549 is injected as input into the pre-filterbank processor 542. In an example, the balance compensation output signals 549 are injected after the pre-filterbank processor 542. In an example, the balance compensation output signals 549 are injected between a pre-filterbank processor 542 and a filterbank 544. In an example, the balance compensation output signals 549 are injected as input into the filterbank 544. In an example, the balance compensation output signals 549 are injected after the filterbank 544. In an example, the balance compensation output signals 549 are injected between the filterbank 544 and a post-filterbank processor 546. In an example, the balance compensation output signals 549 are injected into or after the post-filterbank processor 546. In an example, the balance compensation output signals 549 are injected between the post-filterbank processor 546 and the channel selector 548. In an example, the balance compensation output signals 549 are injected into or after the channel selector 548. In an example, the balance compensation output signals 549 are injected between the channel selector 548 and a mapper and an encoder 550. The injecting can be prior to one or more components of the sound processing path 551, such as prior to one or more of: the pre-filterbank processor 542, the filterbank 544, the post-filterbank processor 546, the channel selector 548, the mapper 550, the encoder 550, other components, or combinations thereof). In an example, the balance compensation output signals 549 are injected into or after the mapper and encoder 550. Where the operation 610 includes operation 612, the injecting can be subsequent to the filtering portion of the sound processing path 551. For example, the injecting can be such that the balance compensation output signals 549 bypass the filtering portion.

The injecting can occur in any of a variety of ways. The injecting can include performing, with respect to the sound input signal 541: weighted or unweighted summation, weighted or unweighted addition, weighted or unweighted superposition, gated selective injection, rules-based selective injection (e.g., injecting responsive to a channel level satisfying a threshold, such as a masker signal level or a post-filterbank processor output level), random injection, or stochastic injection, other techniques, or combinations thereof. The injection of the balance compensation output signal into one or more of the sound processing channels can also be further controlled by time-based rules, such as: simultaneous injection into two or more channels, round robin channel injection, multiplexed selection of channels for injection, random selection, occasional selection of channels for injection, other techniques or combinations thereof. In some examples, the injection completely replaces (e.g., overwrites) the sound signal that was on the channel prior to injection. In some examples, the injection is into a dedicated balance-only portion of the sound processing path 551. In some examples, the injection is into a channel where there was no sound signal (e.g., no prior signal is modified, overwritten, or otherwise interacted with).

Following operation 630, the flow of the process 600 can move to operation 640. Operation 640 can include stimulating tissue based on the sound processing path output signals 559. For example, the sound processing path output signals 559 can be used by the electronics module 210 to provide stimulation using the stimulator assembly 230. Where the sound processing path 551 is disposed in an external component and the stimulator assembly 230 is part of an implantable component 504, then the sound processing path output signals 559 can be transmitted to an implantable component 504 or be generated within an implantable component 504. The operation 640 can include stimulating the tissue using one or more dedicated balance stimulation electrodes based on a portion of the sound processing path output corresponding to the one or more balance compensation output signals.

Although disclosed examples are described herein with respect to particular examples, technology described herein can be applied elsewhere. For example, dysfunctional sensory signals in general can be inhibited with the inhibitor 110 and substituted with signals from the signal generator 120. Other sensory organs than the vestibular system can be inhibited.

As should be appreciated, while particular uses of the technology have been illustrated and discussed above, the disclosed technology can be used with a variety of devices in accordance with many examples of the technology. The above discussion is not meant to suggest that the disclosed technology is only suitable for implementation within systems akin to that illustrated in the figures. For examples, while certain technologies described herein were primarily described in the context of auditory prostheses (e.g., cochlear implants), technologies disclosed herein are applicable to medical devices generally (e.g., medical devices providing pain management functionality or therapeutic electrical stimulation, such as deep brain stimulation). In general, additional configurations can be used to practice the processes and systems herein and/or some aspects described can be excluded without departing from the processes and systems disclosed herein.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and processes to the particular aspects described. Accordingly, additional configurations can be used to practice the methods and systems herein and/or some aspects described can be excluded without departing from the methods and systems disclosed herein.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure. Further, the disclosed processes can be repeated.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

What is claimed is:

1. A method comprising:
selecting a recipient having a balance disorder;
adjusting at least one of the recipient's vestibular system function or the recipient's perception of vestibular system function; and
bypassing the recipient's vestibular system to compensate for the balance disorder by providing a balance compensation output signal to the recipient via one or more non-vestibular sensory channels of the recipient after or while the recipient's vestibular system function or the recipient's perception of vestibular system function is adjusted.

2. The method of claim 1, wherein bypassing the recipient's vestibular system to compensate the balance disorder comprises:
inhibiting the recipient's vestibular system.

3. The method of claim 2, wherein inhibiting the recipient's vestibular system includes applying electrical stimulation to an otolith region or semicircular canals of the recipient.

4. The method of claim 2, further comprising:
ceasing inhibiting the recipient's vestibular system; and
providing another balance compensation output signal while the inhibiting is ceased.

5. The method of claim 1, wherein the balance compensation output signal encodes data regarding rotation about pitch axis using a first characteristic and data regarding rotation about a roll axis using a second characteristic.

6. The method of claim 1, wherein bypassing the recipient's vestibular system to compensate for the balance disorder comprises:
deactivating tissue associated with the vestibular system.

7. The method of claim 1, wherein bypassing the recipient's vestibular system to compensate for the balance disorder comprises:
ablating tissue associated with the vestibular system.

8. The method of claim 1, further comprising providing a pharmacological agent to the recipient.

9. The method of claim 1, wherein providing the balance compensation output signal includes causing a hearing percept in the recipient.

10. The method of claim 9, wherein causing the hearing percept in the recipient includes electrically stimulating a cochlea of the recipient using a dedicated electrode of an auditory prosthesis.

11. The method of claim 1, wherein the one or more non-vestibular sensory channels include: an auditory sensory channel, a tactile sensory channel, or a visual sensory channel.

12. The method of claim 1, wherein providing the balance compensation output signal to the recipient via the one or more non-vestibular sensory channels includes:
encoding data regarding rotation about a roll axis using a first characteristic; and
encoding data regarding rotation about a pitch axis using a second characteristic,
wherein the first and second characteristics are selected from a group consisting of loudness, pitch, stimulation frequency, melody, rhythm, stereo effect, and location.

13. The method of claim 1, wherein bypassing the recipient's vestibular system to compensate for the balance disorder comprises:
delivering electrical stimulation at less than approximately 1 KHz.

14. The method of claim 1, wherein bypassing the recipient's vestibular system to compensate for the balance disorder comprises:
delivering electrical stimulation at approximately 500 Hz.

15. The method of claim 1, wherein bypassing the recipient's vestibular system to compensate for the balance disorder comprises:
delivering electrical stimulation at approximately 900 Hz.

16. An apparatus, comprising:
a first implantable stimulation assembly comprising a stimulation set of one or more electrodes configured to stimulate cochlea tissue of a recipient;
a second implantable stimulation assembly comprising a set of one or more electrodes configured to stimulate vestibular tissue of the recipient;
a vestibular signal generator configured to provide stimulation signals to the second implantable stimulation assembly to stimulate the recipient's vestibular tissue; and
a balance signal generator configured to generate one or more balance compensation output signals that bypass the recipient's vestibular system and cause stimulation via the first implantable stimulation assembly after or while the vestibular tissue is stimulated by the second implantable stimulation assembly.

17. The apparatus of claim 16, further comprising: a sound processing path configured to convert a sound input signal into a sound processing path output signal to cause stimulation via the first implantable stimulation assembly.

18. The apparatus of claim 16, further comprising a vestibular inhibitor signal generator configured to provide stimulation signals to the second implantable stimulation assembly to inhibit the recipient's vestibular system.

19. The apparatus of claim 16, wherein the balance signal generator is configured to generate the one or more balance compensation output signals such that the one or more balance compensation output signals encode balance information regarding rotation about pitch axis using a first characteristic and balance information regarding rotation about a roll axis using a second characteristic.

20. The apparatus of claim 19, wherein the first and second characteristics are selected from a group consisting of loudness, pitch, stimulation frequency, melody, rhythm, stereo effect, and location.

21. The apparatus of claim 16, wherein the balance signal generator is configured to generate one or more balance compensation output signals that deactivate tissue associated with the recipient's vestibular system.

22. The apparatus of claim 16, wherein the balance signal generator is configured to generate one or more balance compensation output signals that ablate tissue associated with the recipient's vestibular system.

23. The apparatus of claim 16, further comprising a component configured to provide a pharmacological agent to the recipient.

* * * * *